(12) United States Patent
White et al.

(10) Patent No.: US 9,381,246 B2
(45) Date of Patent: Jul. 5, 2016

(54) CANCER THERAPY

(71) Applicant: TriAct Therapeutics, Inc., San Francisco, CA (US)

(72) Inventors: Thomas F. White, San Francisco, CA (US); Dan Hoth, San Francisco, CA (US)

(73) Assignee: Triact Therapeutics, Inc., San Francisco, CA (US)

( * ) Notice: Subject to any disclaimer, the term of this patent is extended or adjusted under 35 U.S.C. 154(b) by 0 days.

(21) Appl. No.: 14/481,837

(22) Filed: Sep. 9, 2014

(65) Prior Publication Data

US 2015/0071919 A1 Mar. 12, 2015

Related U.S. Application Data

(60) Provisional application No. 61/875,502, filed on Sep. 9, 2013.

(51) Int. Cl.

| | |
|---|---|
| *A61K 31/282* | (2006.01) |
| *A61K 31/403* | (2006.01) |
| *A61K 45/06* | (2006.01) |
| *A61K 33/24* | (2006.01) |
| *A61K 31/517* | (2006.01) |
| *A61K 31/5377* | (2006.01) |
| *A61K 31/506* | (2006.01) |

(Continued)

(52) U.S. Cl.
CPC .............. *A61K 45/06* (2013.01); *A61K 31/282* (2013.01); *A61K 31/403* (2013.01); *A61K 31/47* (2013.01); *A61K 31/506* (2013.01); *A61K 31/517* (2013.01); *A61K 31/53* (2013.01); *A61K 31/5377* (2013.01); *A61K 33/24* (2013.01)

(58) Field of Classification Search
CPC .... A61K 31/282; A61K 31/403; A61K 45/06
USPC ........................................................ 514/183
See application file for complete search history.

(56) References Cited

U.S. PATENT DOCUMENTS

| 2,644,822 A | 7/1953 | Pearl et al. |
| 4,659,695 A | 4/1987 | Labrie |

(Continued)

FOREIGN PATENT DOCUMENTS

| DE | 19629652 | 1/1998 |
| EP | 520722 | 12/1992 |

(Continued)

OTHER PUBLICATIONS

U.S. Appl. No. 14/261,810, White et al, filed Apr. 25, 2014.*

(Continued)

*Primary Examiner* — Kamal Saeed
*Assistant Examiner* — Janet L Coppins
(74) *Attorney, Agent, or Firm* — Wilson Sonsini Goodrich & Rosati

(57) ABSTRACT

The present application relates to compositions and methods for treating a proliferative disorder by administering to a subject a pharmaceutical composition of a dual kinase inhibitor. Catecholic butanes cane serve as dual kinase inhibitors for purposes of methods described herein. Patients to be treated include those that have been treated with Tarceva or other therapeutic compounds and relapsed or are resistant to treatment. The compounds described herein may exhibit a synergistic effect when administered with another agent.

15 Claims, 27 Drawing Sheets

(51) Int. Cl.
*A61K 31/47* (2006.01)
*A61K 31/53* (2006.01)

(56) References Cited

U.S. PATENT DOCUMENTS

| | | |
|---|---|---|
| 4,683,202 A | 7/1987 | Mullis |
| 4,843,155 A | 6/1989 | Chomczynski |
| 4,868,103 A | 9/1989 | Stavrianopoulos |
| 4,946,778 A | 8/1990 | Ladner et al. |
| 5,008,294 A | 4/1991 | Neiss et al. |
| 5,541,232 A | 7/1996 | Howell et al. |
| 5,624,803 A | 4/1997 | Noonberg et al. |
| 5,631,169 A | 5/1997 | Lakowicz et al. |
| 5,650,415 A | 7/1997 | Tang et al. |
| 5,656,643 A | 8/1997 | Spada et al. |
| 5,747,498 A | 5/1998 | Schnur et al. |
| 5,789,427 A | 8/1998 | Chen et al. |
| 5,854,033 A | 12/1998 | Lizardi |
| 5,861,268 A | 1/1999 | Tang et al. |
| 5,981,732 A | 11/1999 | Cowsert |
| 6,046,321 A | 4/2000 | Cowsert |
| 6,107,091 A | 8/2000 | Cowsert |
| 6,180,603 B1 | 1/2001 | Frey, II |
| 6,191,169 B1 | 2/2001 | Nadler et al. |
| 6,291,524 B1 | 9/2001 | Huang et al. |
| 6,331,526 B1 | 12/2001 | Baserga et al. |
| 6,337,338 B1 | 1/2002 | Kozlowski et al. |
| 6,365,354 B1 | 4/2002 | Bennett et al. |
| 6,410,323 B1 | 6/2002 | Roberts et al. |
| 6,417,234 B1 | 7/2002 | Huang et al. |
| 6,437,105 B1 | 8/2002 | Priebe et al. |
| 6,506,559 B1 | 1/2003 | Fire et al. |
| 6,566,131 B1 | 5/2003 | Cowsert |
| 6,566,135 B1 | 5/2003 | Watt |
| 6,573,099 B2 | 6/2003 | Graham |
| 6,960,474 B2 | 11/2005 | Salvati et al. |
| 7,081,454 B2 | 7/2006 | Wittman et al. |
| 7,189,716 B2 | 3/2007 | Beaulieu et al. |
| 7,232,826 B2 | 6/2007 | Velaparthi et al. |
| 8,710,104 B2 * | 4/2014 | White et al. .............. 514/734 |
| 2004/0005593 A1 | 1/2004 | Lorens |
| 2004/0018191 A1 | 1/2004 | Wang et al. |
| 2004/0175756 A1 | 9/2004 | Kolkman et al. |
| 2004/0209930 A1 | 10/2004 | Carboni et al. |
| 2005/0037421 A1 | 2/2005 | Honda et al. |
| 2005/0048512 A1 | 3/2005 | Kolkman et al. |
| 2005/0048647 A1 | 3/2005 | Taira et al. |
| 2005/0053973 A1 | 3/2005 | Kolkman et al. |
| 2005/0060771 A1 | 3/2005 | Farmer |
| 2005/0089932 A1 | 4/2005 | Kolkman et al. |
| 2005/0136063 A1 | 6/2005 | Wang et al. |
| 2005/0164301 A1 | 7/2005 | Kolkman et al. |
| 2005/0221384 A1 | 10/2005 | Kolkman et al. |
| 2006/0141029 A1 | 6/2006 | Heller et al. |
| 2006/0151574 A1 | 7/2006 | Herget et al. |
| 2007/0065858 A1 | 3/2007 | Haley |
| 2007/0099847 A1 | 5/2007 | Goldfine et al. |
| 2008/0096967 A1 | 4/2008 | Lopez et al. |
| 2008/0113874 A1 | 5/2008 | Bunn |
| 2008/0207532 A1 | 8/2008 | Huang et al. |
| 2008/0214584 A1 | 9/2008 | Ohta et al. |
| 2010/0256232 A1 * | 10/2010 | White et al. |
| 2014/0235714 A1 | 8/2014 | White et al. |

FOREIGN PATENT DOCUMENTS

| | | |
|---|---|---|
| EP | 566226 | 10/1993 |
| EP | 682027 | 11/1995 |
| EP | 787772 | 8/1997 |
| EP | 837063 | 4/1998 |
| EP | 0404097 | 6/2009 |
| EP | 2961412 A1 | 1/2016 |
| JP | 2-49731 A | 3/1990 |
| JP | 07-133280 | 5/1995 |
| JP | 7-238037 A | 9/1995 |
| JP | 8-337510 A | 12/1996 |
| WO | WO-92-20642 A1 | 11/1992 |
| WO | WO-93-11161 A1 | 6/1993 |
| WO | WO-95-09847 A1 | 4/1995 |
| WO | WO-95-19774 A1 | 7/1995 |
| WO | WO-95-19970 A1 | 7/1995 |
| WO | WO-96-30347 A1 | 10/1996 |
| WO | WO-96-31510 A1 | 10/1996 |
| WO | WO-96-33980 A1 | 10/1996 |
| WO | WO-96-37201 | 11/1996 |
| WO | WO-97-02266 A1 | 1/1997 |
| WO | WO-97-13771 A1 | 4/1997 |
| WO | WO-97-19065 A1 | 5/1997 |
| WO | WO-97-27199 A1 | 7/1997 |
| WO | WO-97-28161 A1 | 8/1997 |
| WO | WO-97-30034 A1 | 8/1997 |
| WO | WO-97-30044 A1 | 8/1997 |
| WO | WO-97-32880 A1 | 9/1997 |
| WO | WO-97-32881 A1 | 9/1997 |
| WO | WO-97-34895 A1 | 9/1997 |
| WO | WO-97-38983 A1 | 10/1997 |
| WO | WO-97-38994 A1 | 10/1997 |
| WO | WO-97-49688 A1 | 12/1997 |
| WO | WO-98-02434 A1 | 1/1998 |
| WO | WO-98-02437 A1 | 1/1998 |
| WO | WO-98-02438 A1 | 1/1998 |
| WO | WO-98-07726 A1 | 2/1998 |
| WO | WO-98-14449 A1 | 4/1998 |
| WO | WO-98-14451 A1 | 4/1998 |
| WO | WO-98-17662 A1 | 4/1998 |
| WO | WO-98-33787 A1 | 8/1998 |
| WO | WO-99-07701 A1 | 2/1999 |
| WO | WO-99-32619 A1 | 7/1999 |
| WO | WO-99-35132 A1 | 7/1999 |
| WO | WO-99-35146 A1 | 7/1999 |
| WO | WO-00-17203 A1 | 3/2000 |
| WO | WO-00-35455 | 6/2000 |
| WO | WO-00-35455 A1 | 6/2000 |
| WO | WO-00-71129 A1 | 11/2000 |
| WO | WO-01-36646 A1 | 5/2001 |
| WO | WO-01-68836 A2 | 9/2001 |
| WO | WO-02-092599 | 11/2002 |
| WO | WO-02-092599 A1 | 11/2002 |
| WO | WO-02-102804 | 12/2002 |
| WO | WO-02-102804 A1 | 12/2002 |
| WO | WO-02-102805 A1 | 12/2002 |
| WO | WO-03-018021 A1 | 3/2003 |
| WO | WO-03-018022 | 3/2003 |
| WO | WO-03-018022 A1 | 3/2003 |
| WO | WO-03-024967 | 3/2003 |
| WO | WO-03-024967 A2 | 3/2003 |
| WO | WO-03-035614 A2 | 5/2003 |
| WO | WO-03-035615 A2 | 5/2003 |
| WO | WO-03-035616 | 5/2003 |
| WO | WO-03-035616 A2 | 5/2003 |
| WO | WO-03-035619 A1 | 5/2003 |
| WO | WO-03-048133 A1 | 6/2003 |
| WO | WO-03-068265 A1 | 8/2003 |
| WO | WO-2004-030625 | 4/2004 |
| WO | WO-2005-037836 A2 | 4/2005 |
| WO | WO-2005-082415 | 9/2005 |
| WO | WO-2006-041902 A2 | 4/2006 |
| WO | WO-2006-138729 | 12/2006 |
| WO | WO-2008-089388 A2 | 7/2008 |
| WO | WO-2009-108857 | 9/2009 |
| WO | WO-2010-054264 | 5/2010 |
| WO | WO-2014134202 A1 | 9/2014 |
| WO | WO-2015035410 A1 | 3/2015 |

OTHER PUBLICATIONS

Agrawal et al., "Overview of tyrosine kinase inhibitors in clinical breast cancer" Endocrine Related Cancer (Mar. 2005) 12:S135-S144.
Albert et al., "Pteridine Studies,. Part XXXIX. Pteridines Unsubstituted in the 4-Position; a New Synthesis from Pyrazines, via 3,4-Dihydropteridines," J. Chem. Soc. 11:1540-1547 (1970).
Avrameas, "Peroxidase labelled antibody and Fab conjugates with enhanced intracellular penetration," Immunochemistry 8:1175-1179 (1975).

(56) References Cited

OTHER PUBLICATIONS

Barany, "Genetic disease detection and DNA amplification using cloned thermostable ligase," PNAS USA 88:189-193 (1991).
Baserga, "The IGF-1 Receptor in Cancer Research," Exp. Cell. Res. 253:1-6 (1999).
Baserga, "The insulin-like growth factor I receptor: a key to tumor growth?" Cancer Res Jan. 15, 1995;55.
Berge et al., J. Pharm. Sci. 66:1-19 (1977).
Bird et al., Science 242:423-426 (1988).
Blum et al., "Development of New Insulin-like Growth Factor-1 Receptor Kinase Inhibitors Using Catechol Mimics" The Journal of Biological Chemistry, 278(42):40442-40454 (2003).
Blum et al., "Substrate Competitive Inhibitors of IGF-1 Receptor Kinase" Biochemistry, 39:15705-15712 (2000).
Boston-Howes et al., "Nordihydroguaiaretic acid increases glutamate uptake in vitro and in vivo: Therapeutic implications for amyotrophic lateral sclerosis," Exp. Neurol. 213(1):229-237 (2008).
Brem and Gabikian, "Biodegradable polymer implants to treat brain tumors," J. Controlled Release 74:63-67 (2001).
Brummelkamp et al., "A System for Stable Expression of Short Interfering RNAs in Mammalian Cells," Science 296:550-553 (2002).
Burfeind, RNA to the type I insulin-like growth factor receptor suppresses tumor growth and prevents invasion by prostate cancer cells in vivo. Proc Natl Acad Sci USA 1996;vol. 93, Iss 14:7263-8.
CA 2,742,986 Office action mailed Oct. 25, 2013.
CA 2,742,986 Office action mailed Sep. 11, 2012.
Camirand and Pollak, "Co-targeting IGF-1R and c-kit: synergistic inhibition of proliferation and induction of apoptosis in H209 small cell lung cancer cells," Brit. J. Cancer 90:1825-1829 (2004).
Camp et al. (Clin Cancer Res 11:397-405, 2005).
Chang et al., "Nonreceptor Tyrosine Kinases in Prostate Cancer" Neoplasia, 9(2):90-100 (Feb. 2007).
Chang et al., "Experimentally-induced prostatic hyperplasia in young beagles: a model to evaluate the chemotherapeutic effects of gossypol," Res Comm Mol Path Pharmacol 92(3):341-360 (1996).
CN200980126999.1 Decision of Rejection dated Jul. 7, 2014.
Cole et al., "The EBV-Hybridoma Technique and Its Application to Human Lung Cancer," Monoclonal Antibodies and Cancer Therapy, Alan R. Liss Inc. 1985, pp. 77-96.
Cote et al., "Generation of human monoclonal antibodies reactive with cellular antigens," PNAS USA 80:2026-2030 (1983).
Diaz et al., "Management of Androgen-Independent Prostate Cancer" Cancer Control, 11(6):364-373 (Nov./ Dec. 2004).
Doctor's Guide, Sep. 28, 1998, pp. 1-3.
Domin et al., "Preferential inhibition of platelet-derived growth factor-stimulated DNA synthesis and protein tyrosine phosphorylation by nordihydroguaiaretic acid," J. Biol. Chem. 269(11):8260-8267 (1994).
Earashi et al., "Effects of Eicosanoid Synthesis Inhibitors on the in vitro Growth and Prostaglandin E and Leukotriene B. Secretion of a Human Breast Cancer Cell Line" Oncology, 52:150-155 (1995).
Elbashir et al., "Duplexes of 21-nucleotide RNAs mediate RNA interference in cultured mammalian cells," Nature 411:494-498 (2001).
Eli. "Ketoconazole binds to the human androgen receptor." Horm. Metabol. Res. 1992, 24(8): 367-370.
Engvall, "Enzyme-linked immunosorbent assay (ELISA) Quantitative assay of immunoglobulin G," Immunochemistry 8:871-874 (1971).
Fleming, "Pharmacokinetics of the Carmustine Implant," Clin. Pharmacokinet. 41:403-419 (2002).
Fu et al., "New polymeric carriers for controlled drug delivery following inhalation or injection," Biomaterials 23:4425-4433 (2002).
Garcia-Echeverria et al., "In vivo antitumor activity of NVP-AEW541-A novel, potent, and selective inhibitor of the IGF-1R kinase," Cancer Cell 5:231-239 (2004).
Gavezzotti, "Are Crystal Structures Predictable?", Accounts of Chemical Research, vol. 27, pp. 309-314 (1994).

Gendreau, et al. "Inhibition of the T790M Gatekeeper Mutant of the Epidermal Growth Factor Receptor by EXEL-7647." Clin Cancer Res 2007;13:3713-3723.
Goldstein et al., Biological Efficacy of a Chimeric Antibody to the Epidermal Growth Factor Receptor in a Human Tumor Xenograft Model,: Clin. Cancer Res. 1:1311-1318 (1995).
Greco et al., "The Search for Syngergy: A Critical Review from a Response Surface Perspective" Pharmacological Reviews 47(2):331-385 (1995).
Guatelli et al., "Isothermal, in vitro amplification of nucleic acids by a multienzyme reaction modeled after retroviral replication," PNAS USA 87:1874-1878 (1990).
Gura, "Cancer Models: Systems for Identifying New Drugs Are Often Faulty" Science (Nov. 1997) 278(5340):1041-42.
Hage, "Recent advances in chromatographic and electgrophoretic methods for the study of drug-protein interactions," Chromatogr. B. Biomed Sci. Appl. 699(1-2):499-525 (1997).
Hannon, "RNA interference," Nature 418:244-251 (2002).
Heegaard, "Capillary electrophoresis for the study of affinity interactions," J. Mol. Recognit. WInter 11(1-6):141-148 (1998).
Holliger et al., "Diabodies: Small bivalent and bispecific antibody fragments," PNAS USA 90:6444-6448 (1993).
Huang et al. Nordihydroguaiaretic acid-induced Ca2+ handling and cytotoxicity in human prostate cancer cells. Life Sciences, 75, 2004, 2341-2351.
Huang et al., "Epidermal Growth Factor Receptor Blockade with C225 Modulates Proliferation, Apoptosis, and Radiosensitivity in Squamous Cell Carcinomas of the Head and Neck," Cancer Res. 15:59(8):1935-1940 (1999).
Huse et al., Science 246:1275-1281 (1989).
Huston et al., PNAS USA 85:5879-5883 (1988).
Ibrahim and Yee, "Insulin-Like Growth Factor-1 and Breast Cancer Therapy," Clin. Cancer Res. 11:944s-950s (2005).
Ishikawa et al., "Enzyme-Labeling of Antibodies and Their Fragments for Enzyme Immunoassay and Immunohistochemical Staining," J. Immunoassay 4(3):209-327 (1983).
Jablonski, "The Preparation of Bacterial Luciferase Conjugates for Immunoassay and Application to Rubella Antibody Detection," Anal. Biochem. 148:199-206 (1985).
Jones et al., Nature 321:522-525 (1986).
Kisielewska et al., "The effect of tyrosine kinase inhibitors, tyrphostins: AG1024 and SU1498, on autocrine growth of prostate cancer cells (DU145)" Folia Histochemica et Cytobiologica, 46(2):185-91 (2008).
Kohler and Milstein, Nature 256:495-497 (1975).
Kozbor et al., "The production of monoclonal antibodies from human lymphocytes," Immunol. Today 4:72-79 (1983).
Kwoh et al., "Transcription-based amplification system and detection of amplified human immunodeficiency virus type 1 with a bead-based sandwich hybridization format," PNAS USA 86:1173-1177 (1989).
Larsson et al., "Role of insulin-like growth factor 2 receptor signalling in cancer," Brit. J. Cancer 92:2097-2101 (2005).
Lee et al., "Expression of small interfering RNAs targeted against HIV-1 rev transcripts in human cells," Nat. Biotech. 20:500-505 (2002).
Lizardi et al., "Exponential amplification of recombinant-RNA hybridization probes," Biotechnology 6:1197-1202 (1988).
McManus and Sharp, "Gene silencing in mammals by small interfering RNAs," Nature Reviews Genetics 3:737-747 (2002).
Meyer et al., "Nordihydroguaiaretic Acid Inhibits Insulin-Like Growth Factor Signaling Growth, and Survival in Human Neuroblastoma Cells" Journal of Cellular Biology, 102(6):1529-1541 (Dec. 2007).
Mitsiades et al., "Inhibition of the insulin-like growth factor receptor-1 tyrosine kinase activity as a therapeutic strategy for multiple myeloma, other hematologic malignancies, and solid tumors," Cancer Cell 5:221-230 (2004).
Miyagishi et al., "Y6 promoter-driven siRNAs with four uridine 3' overhangs efficiently suppress targeted gene expression in mamalian cells," Nat. Biotech. 20:497-500 (2002).

(56) References Cited

OTHER PUBLICATIONS

Modjtahedi et al., "The human EGF receptor as a target for cancer therapy: six new rat mAbs against the receptor on the breast carcinoma MDA-MB 468," Br. J. Cancer 67:247-253 (1993).
Morgillo, et al. Implication of the insulin-like growth factor-IR pathway in the resistance of non-small cell lung cancer cells to treatment with gefitinib. Clin Cancer Res. May 1, 2007;13(9):2795-2803.
Muyldermans et al., "Sequence and structure of VH domain from naturally occurring camel heavy chain immunoglobulins lacking light chains," Protein Engineering 7(9):1129-1133 (1994).
MX/a/2011/004824 office action mailed Sep. 28, 2012.
Nickerson, "In vivo progression of LAPC-9 and LNCaP prostate cancer models to androgen independence is associated with increased expression of insulin-like growth factor I (IGF-I) and IGF-I receptor (IGF-IR) 1." Cancer Res Aug. 15, 2001;61(16):6276-80.
Nicolini et al. Oral low-dose cyclophosphamide in metastatic hormone refractory prostate cancer (MHRPC). Biomedicine & Pharmacotherapy, 58, 2004: 447-450.
Nieto, "Prostate cancer: Re-focusing on androgen receptor signaling." Int J Biochem Cell Biol 2007;39(9):1562-8.
Osborne et al., "Inhibition of Breast Cancer Cell Growth in Vitro by a Tyrosine Kinase Inhibitor," Cancer Res. 52:3636-3641 (1992).
Osbourn et al., Nat. Biotech. 16:778 (1998).
Paddison et al., "Short hairpin RNAs (shRNAs) induce sequence-specific silencing in mammalian cells," Genes Dev. 16:948-958 (2002).
Pao, et al., "Acquired Resistance of Lung Adenocarcinomas to Gefitinib or Erlotinib Is Associated with a Second Mutation in the EGFR Kinase Domain." PLoS Med 2(3): e73; pp. 1-10. doi:10.1371/journal.pmed.0020073.
Parrizas et al., "Specific Inhibition of Insulin-Like Growth Factor-1 and Insulin Receptor Tyrosine Kinase Activity and Biological Function by Tyrphostins," Endocrinology 138:1427-1433 (1997).
Paul et al., "Effective expression of small interfering RNA in human cells," Nat. Biotech. 20:505-508 (2002).
PCT/US09/63646 International Search Report dated Feb. 19, 2010.
PCT/US09/63646 IPRP dated May 10, 2011.
PCT/US09/63646 Written Opinion dated Jul. 5, 2011.
Pirtskhalaishvilli et al. "The treatment of prostate cancer: an overview of current options." Cancer Practice, vol. 9, No. 6, Nov./Dec. 2001.
Pluckthun in Handbook of Experimental Pharmacology vol. 113, Rosenburg and Moore eds., Springer-Verlag, NY, pp. 269-315 (1994).
Pollak, "Insulin-like growth factors and prostate cancer 115." Epidemiol Rev 2001;23(1):59-66.
Presta, Curr. Op. Struct. Biol. 2:593-596 (1992).
"Protein kinase inhibitor," Wikipedia, The Free Encyclopedia http://en.wikipedia.org/wiki/Protein_kinase_inhibitor (downloaded Jan. 30, 2010).
Reichmann et al., "Reshaping human antibodies for therapy," Nature 332:323-329 (1988).
Rheinwald et al., "Epidermal growth factor and the multiplication of cultured human epidermal keratinocytes," Nature 265:421-424 (1977).
Rivas, "New developments in the study of biomolecular associations via sedimentation equilibrium," Trends Biochem. Sci. 18(8):284-287 (1993).
Robertson et al., "Overview of tyrosine kinase inhibitors in clinical breast cancer," Endocrine-Related Cancer 12:S135-S144 (2005).
Robins et al., "Synthesis and anticancer activity of nordihydroguaiaretic acid (NDGA) and analogues," Anti-Cancer Drug Design 16:261-270 (2001).
Rodeck et al., "EGF-R dependent regulation of keratinocyte survival," J. Cell Science 110:113-121 (1997).
Rowe et al., "Nordihydroguaiaretic acid, a cytotoxic insulin-like growth factor-I receptor/HER2 inhibitor in trastuzumab-resistant breast cancer," Mol. Cancer Therapeutics 7(7):1900-1908 (2008).
Rozengurt et al., "Preferential Inhibition of Platelet-derived Growth Factor-stimulated DNA Synthesis and Protein Tyrosine Phosphorylation by Nordihydroguaiaretic Acid," J. Biol. Chem. 269(11):8260-8267 (1994).
Ryan et al. "A pilot dose-escalation study of the effects of nordihydroguareacetic acid on hormone and prostate specific antigen levels in patients with relapsed prostate cancer" BJU International, 101(4):436-439 (Feb. 2008).
Ryan et al., "Androgen-independent prostate cancer: target evolution and disease dynamics" Drug Discovery Today: Disease Mechanisms, Elsevier, 1(2):223-228 (Nov. 1, 2004).
Ryan et al., "Inhibitory Effects of Nordihydroguaiaretic Acid (NDGA) on the IGF-1 Receptor and Androgen Dependent Growth of LAPC-4-Prostate Cancer Cells" The Prostate, 68:1232-1240 (2008).
Seufferlein et al., "Mechanisms of nordiydroguaiaretic acid-induced growth inhibition and apoptosis in human cancer cells," Br. J. Cancer 86:1188-1196 (2002).
Sharifi et al. "Leuprolide acetate (30 mg depot every four months) in the treatment of advanced prostate cancer." Urology, 51: 271-276, 1998.
Sherwood et al., "Selective inhibition of heregulin-dependent tyrosin phosphorylation and cellular signaling through erbB2, erbB3 and erbB4 by PD 158780 and a new irreversible inhibitor, PD 183805," Proc. Am. Assoc. Cancer Res. 40:723 (1999).
Silverman et al., "Corrigendum: Multivalent avimer proteins evolved by exon shuffling of a family of human receptor domains," Nat. Biotech.. 24:220 (2006).
Silverman et al., "Multivalent avimer proteins evolved by exon shuffling of a family of human receptor domains," Nat. Biotech. 23:1493-1494 (2005).
Sjolander, "Integrated Fluid Handling System for Biomolecular Interaction Analysis," Anal. Chem. 63:2338-2345 (1991).
Szabo et al., "Surface plasmon resonance and its use in biomolecular interaction analysis (BIA)," Curr. Op. Struct. Biol. 5:699-705 (1995).
Taichman et al. "The evolving biology and treatment of prostate cancer." The Journal of Clinical Investigation. vol. 117, No. 9, 2351-2361, Sep. 2007.
Teramoto et al., "Inhibitory Effect of Anti-Epidermal Growth Factor Receptor Antibody on a Human Gastric Cancer," Cancer 77:639-645 (1996).
Therasse et al., J. Natl. Cancer Inst. 92(3):205-216 (2000).
Traxler, "Use of a Pharmacophore Model for the Design of EGFR Tyrosine Kinase Inhibitors: Isoflavones and 3-Phenyl-4(1H)-quinolones," J. Med. Chem. 42:1018-1026 (1999).
Tuschl et al., "Expanding small RNA interference," Nat. Biotech. 20:446-448 (2002).
Tuschl et al., "Targeted mRNA degradation by double-stranded RNA in vitro," Genes Dev. 13(24):3191-3197 (1999).
TW 098137952 Office action mailed Jun. 4, 2012.
U.S. Appl. No. 11/552,686 Office Action mailed Dec. 8, 2010.
U.S. Appl. No. 11/552,686 Office Action mailed Jul. 20, 2011.
U.S. Appl. No. 11/552,686 Office Action mailed May 29, 2009.
U.S. Appl. No. 11/552,686 Office Action mailed Nov. 24, 2008.
U.S. Appl. No. 12/434,071 Office action mailed Aug. 15, 2013.
U.S. Appl. No. 12/434,071 Office action mailed Aug. 9, 2012.
U.S. Appl. No. 12/434,071 Office action mailed Jan. 29, 2013.
U.S. Appl. No. 12/434,071 Office action mailed Jul. 14, 2011.
U.S. Appl. No. 12/434,071 Office action mailed Nov. 8, 2011.
U.S. Appl. No. 12/614,283 Office action mailed Jan. 10, 2013.
U.S. Appl. No. 12/614,283 Office action mailed Jul. 3, 2013.
U.S. Appl. No. 12/614,283 Office action mailed May 2, 2012.
Vaughan et al., "Human antibodies by design," Nature Biotech. 16:535-539 (1998).
Vippagunta et al, "Crystalline Solids", Advanced Drug Delivery Reviews, vol. 48, pp. 3-26 (2001).
Ward et al., Nature 341:544-546 (1989).
Wilkinson et al. "An evaluation of intermediate dose ketoconazole in hormone refractory prostate cancer." European Urology, 45:581-585 (2004).

(56) References Cited

OTHER PUBLICATIONS

Woodburn et al., "ZD1839, an epidermal growth factor tyrosine kinase inhibitor selected for clinical development," Proc. Am. Assoc. Cancer Res. 38:633 (1997).

Yang, et al., "Eradication of Established Tumors by a Fully Human Monoclonal Antibody to the Epidermal Growth Factor Receptor without Concomitant Chemotherapy," Cancer Res. 59:1236-1243 (1999).

Fleming et al., Synergistic inhibition of ErbB signaling by combined treatment with seliciclib and ErbB-Trageting agents. Clinical Cancer Research, 14(13): 4326-4335 (2008).

Gerber et al., ALK inhibition for non-small cell lung cancer: From discovery to therapy in record time. Cancer Cell, 18(6): 548-551 (2010).

Merck Manual, p. 800-803 (1992).

Neoptolimos et al., Adjuvant therapy in pancreatic cancer: historical and current perspectives, Annals of Oncology, 14:675-692 (2003).

Ortiz-Ferron et al., Roscovitine sensitizes breast cancer cells to TRAIL-induced apoptosis through a pleiotropic mechanism. Cell Research, 18:664-676 (2008).

PCT/US09/002781 IPRP dated Nov. 9, 2010.

PCT/US09/002781 ISR dated Sep. 29, 2009.

PCT/US09/002781 WO dated Sep. 29, 2009.

PCT/US2014/054832 ISR and WO dated Dec. 22, 2014.

Sharma et al., In the clinic: ongoing clinical trials evaluating c-MET inhibiting drugs. Therapeutic Advances in Medical Oncology, 3(1): 537-550 (2011).

U.S. Appl. No. 13/399,031 Office Action mailed Jul. 25, 2012.

U.S. Appl. No. 14/261,810 Office Action dated Dec. 3, 2015.

\* cited by examiner

A.

B.

A.

B.

A.

B.

A.

B.

A.

B.

A.

B.

A.

B.

A.

B.

A.

B.

A.

B.

A.

B.

A.

B.

A.

B.

CANCER THERAPY

CROSS REFERENCE

This application claims the benefit of U.S. Provisional Application No. 61/875,502, filed Sep. 9, 2013, which is hereby incorporated by reference in its entirety.

BACKGROUND OF THE INVENTION

Proliferative diseases are a serious threat to modern society. Cancerous growths, including malignant cancerous growth, pose serious challenges for modern medicine due to their unique characteristics. Their characteristics include uncontrollable cell proliferation resulting in, for example, unregulated growth of malignant tissue, an ability to invade local and even remote tissues, lack of differentiation, lack of detectable symptoms and most significantly, the lack of effective therapy and prevention.

Cancer can develop in any tissue of any organ at any age. The etiology of cancer is not clearly defined but mechanisms such as genetic susceptibility, chromosome breakage disorders, viruses, environmental factors and immunologic disorders have all been linked to a malignant cell growth and transformation. Cancer encompasses a large category of medical conditions, affecting millions of individuals worldwide. Cancer cells can arise in almost any organ and/or tissue of the body. Cancer develops when cells in a part of the body begin to grow or differentiate out of control. All cancer types begin with the out-of-control growth of abnormal cells.

Worldwide, more than 10 million people are diagnosed with cancer every year and it is estimated that this number will grow to 15 million new cases every year by 2020. Cancer causes six million deaths every year or 12% of the deaths worldwide.

SUMMARY OF THE INVENTION

The methods described herein provide the first potential therapy for cancer relapse patients, including, for example, patients refractory to TARCEVA® and IRESSA® treatment for which there are no approved therapies.

Provided herein is a method of treating a patient in need thereof, comprising administering to the patient a therapeutically effective amount of a catecholic butane and a therapeutically effective amount of a platinum-containing anti-cancer drug, an EGFR receptor inhibitor, a Met inhibitor, an IGF-1 inhibitor, or an Alk inhibitor, wherein administration of the combination of the catecholic butane and the platinum-containing anti-cancer drug, EGFR receptor inhibitor, Met inhibitor, IGF-1 inhibitor, or Alk inhibitor, provides a synergistic therapeutic effect compared to each compound alone, and wherein the catecholic butane inhibits the tyrosine kinase activity of both IGF-1R and EGFR.

In one embodiment, the platinum-containing anti-cancer drug is cisplatin, carboplatin or oxaliplatin. In one embodiment, the EGFR receptor inhibitor is Erlotinib (TARCEVA®), Gefitinib (IRESSA®), Cetuximab, Afatinib, Rociletinib or AZD9291. In one embodiment, the Met inhibitor is Cabozantinib, Tivantinib, Foretinib, INCB28060, AMG-458, PF-04217903, PF-02341066, E7050, MK-2461, BMS-777607 or JNJ-38877605. In one embodiment, the Alk inhibitor is Crizotinib Ceritinib, Alectinib or CH5424802.

The proliferative disease can be a malignant, pre-malignant or benign cancer. In one embodiment, the cancer is a solid tumor, a lymphoma or a leukemia.

A cancer may be selected from the group consisting of brain tumor, carcinoma, basalioma, teratoma, retinoblastoma, choroidea melanoma, seminoma, sarcoma, plasmocytoma, head and neck tumor, liver tumor, kidney tumor, renal cell tumor, squamous cell carcinoma, uterine tumor, bone tumor, prostate tumor, breast tumor, bladder tumor, pancreatic tumor, endometrium tumor, squamous cell carcinoma, stomach tumor, gliomas, colorectal tumor, testicular tumor, colon tumor, rectal tumor, ovarian tumor, cervical tumor, eye tumor, central nervous system tumor, thyroid tumor, lung tumor, leukemia or lymphoma, multiple myeloma, skin tumor, a gynecologic tumor, Hodgkin's disease, cancer of the small intestine, cancer of the endocrine system, mesothelioma, cancer of the urethra, cancer of the penis, tumors related to Gorlin's syndrome, and tumor of unknown origin; and metastases thereto.

In one embodiment, the cancer is selected from the group consisting of small cell lung cancer, pancreatic cancer, breast cancer, breast cancer over-expressing Her-2, colon cancer, cervical cancer, neuroblastoma and non-small cell lung cancer.

In another embodiment, the lung cancer is non-small cell lung cancer (NSCLC).

In another embodiment, the cancer is a primary tumor or a metastasis.

A catecholic butane used herein inhibits tyrosine kinase activity of IGF-1R, EGFR, cMet and/or KDR (VEGF2) in certain instances.

The patient may have a proliferative disease that is resistant to Erlotinib (TARCEVA®) or Gefitinib (IRESSA®), or who has relapsed after treatment with Erlotinib (TARCEVA®) or Gefitinib (IRESSA®).

Cancer cells, in some instances, contain an EGFR mutation that confers resistance to Tarceva. In some instances, cancer cells contain a T790M mutation in an ATP binding domain of a receptor tyrosine kinase (RTK). In some instances, cancer cells contain a T854A, D761Y, L747S mutation in a RTK.

In some instances, cancer cells contain a Kras mutation in a receptor tyrosine kinase (RTK). In some non-limiting examples, cancer cells contain a Nearly all KRAS mutations in lung cancer are G12A, G12C, G12D, G12F, or G12V Kras mutation. In other non-limiting examples, cancer cells contain an amplification of c-Met gene.

Provided herein is a method of treating cancer cells that contain a T790M mutation in an ATP binding domain of a receptor tyrosine kinase (RTK) in a patient in need thereof, comprising administering to the patient a therapeutically effective dose of a catecholic butane.

In some instances, cancer cells are resistant to treatment with Erlotinib (TARCEVA®) or Gefitinib (IRESSA®).

In some instances, the catecholic butane inhibits tyrosine kinase activity of IGF-1R, EGFR, cMet and/or KDR (VEGF2).

In some instances, the catecholic butane binds to the substrate-binding domain of the RTK.

The method may further comprise administering to the patient a platinum-containing anti-cancer drug, an EGFR receptor inhibitor, a Met inhibitor, an IGF-1 inhibitor, or an Alk inhibitor. In one embodiment, the platinum-containing anti-cancer drug is cisplatin, carboplatin or oxaliplatin. In one embodiment, the EGFR receptor inhibitor is Erlotinib (TARCEVA®), Gefitinib (IRESSA®), Cetuximab, Afatinib, Rociletnib or AZD9291. In one embodiment, the Met inhibitor is Cabozantinib, Tivantinib, Foretinib, INCB28060, AMG-458, PF-04217903, PF-02341066, E7050, MK-2461, BMS-777607 or JNJ-38877605. In one embodiment, the Alk inhibitor is Crizotinib Ceritinib, Alectinib or CH5424802.

Provided herein is a method of treating a patient that is resistant to Erlotinib (TARCEVA®) or Gefitinib (IRESSA®), comprising administering to the patient a therapeutically effective amount of a catecholic butane, wherein administration of said catecholic butane restores the effectiveness of cisplatin, Erlotinib (TARCEVA®) or Gefitinib (IRESSA®).

The catecholic butane can bind to the substrate-binding domain of a receptor tyrosine kinase (RTK) and induces a conformational change in the RTK.

The method may further comprise administering to the patient a platinum-containing anti-cancer drug, an EGFR receptor inhibitor, a Met inhibitor, an IGF-1 inhibitor, or an Alk inhibitor. In one embodiment, the platinum-containing anti-cancer drug is cisplatin, carboplatin or oxaliplatin. In one embodiment, the EGFR receptor inhibitor is Erlotinib (TARCEVA®), Gefitinib (IRESSA®), Cetuximab, Afatinib, Rociletnib or AZD9291. In one embodiment, the Met inhibitor is Cabozantinib, Tivantinib, Foretinib, INCB28060, AMG-458, PF-04217903, PF-02341066, E7050, MK-2461, BMS-777607 or JNJ-38877605. In one embodiment, the Alk inhibitor is Crizotinib Ceritinib, Alectinib or CH5424802.

In some instances, the catecholic butane comprises a catecholic butane of formula I, pharmaceutically acceptable salts thereof, pharmaceutically acceptable solvates thereof, metabolites thereof, tautomers thereof or prodrugs thereof:

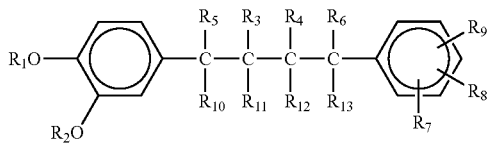

wherein R1 and R2 are independently H, lower alkyl, or lower acyl; R3, R4, R5, R6, R10, R11, R12 and R13 are independently H or lower alkyl; and R7, R8 and R9 are independently H, hydroxy, lower alkoxy or lower acyloxy.

In other instances, the catecholic butane comprises a catecholic butane of formula I, pharmaceutically acceptable salts thereof, pharmaceutically acceptable solvates thereof, metabolites thereof, tautomers thereof or prodrugs thereof:

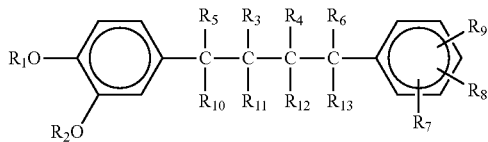

wherein R5, R10, R6, and R13 are independently H; when R3 is H, R11 is lower alkyl; or when R3 is lower alkyl, R11 is H; when R4 is H, R12 is lower alkyl; or when R4 is lower alkyl, R12 is H; two of R7, R8, and R9 are hydroxy, the other is H, and one of the hydroxy groups is in the 3-position and the other hydroxy group is in the 4-position relative to the alkylene substituent.

In other instances, the catecholic butane is selected from the group consisting of NDGA, tetra-O-methyl NDGA; tetraglycinyl NDGA; tetra-dimethylglycinyl NDGA or a salt thereof; or tri-O-methyl NDGA; nordihydroguaiaretic acid tetrapivalate; nordihydroguaiaretic acid tetrapropionate and all optical configurations thereof.

In other instances, the catecholic butane is 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl)butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; 1-(3,4-dihydroxyphenyl)-4-(2,5-dihydroxyphenyl)butane.

In yet other instances, the catecholic butane is nordihydroguaiaretic acid (NDGA).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 13B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 14B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 15B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 20B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 21B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 22B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 23B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 24B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 25B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

FIG. 26B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM.

FIG. 27B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM.

FIG. 28B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM.

FIG. 29B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM.

DETAILED DESCRIPTION OF THE INVENTION

Figure 1:
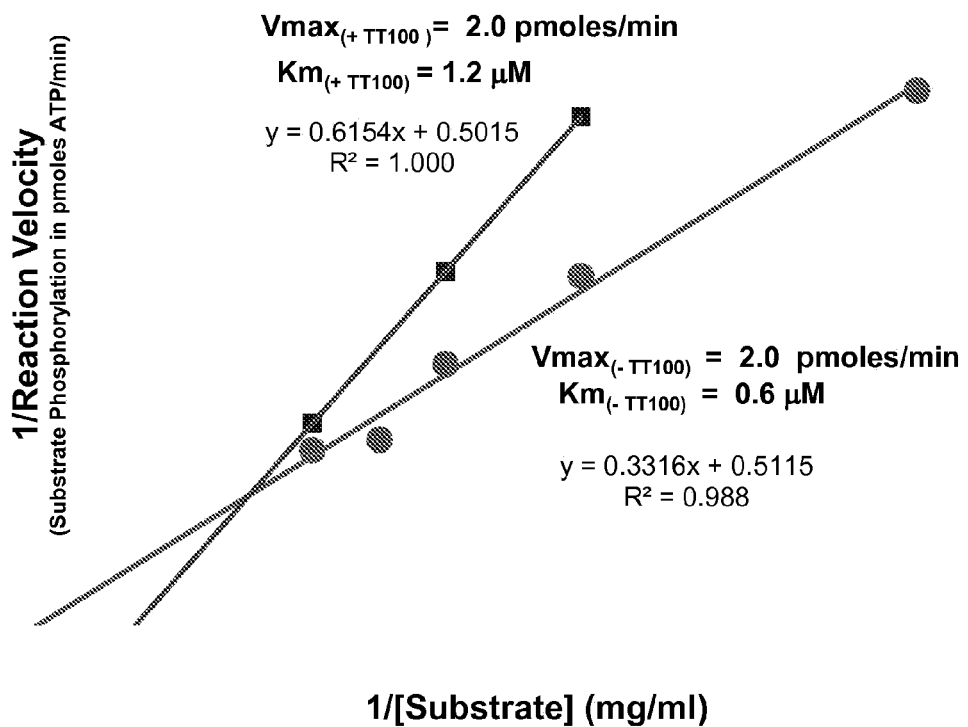
FIG. 1. NDGA Inhibits IGF-1R Substrate Kinase Activity. Tyrosine kinase substrate Glu4: Tyr1 was bound to 96 well plates. Partially purified IGF-1R was added ±20 mg/ml NDGA prior to the addition of 10 nM IGF-1 and 20 µM ATP. Phosphorylation of substrate was determined by anti-phosphotyrosine ELISA**. NDGA displays competition with ATP for activation of the IGF-1R kinase activity. (B) Without NDGA (−TT100): Vmax=2.0 pmoles/min, Km=0.6 µM; with NDGA (+TT100): Vmax=2.0 pmoles/min, Km=1.2 µM.

Diseases to be treated using the methods provided herein are proliferative diseases.

A proliferative disease includes, but is not limited to, a malignant, pre-malignant or benign cancer. Cancers to be treated using the disclosed methods include, for example, a solid tumor, a lymphoma or a leukemia. In one embodiment, a cancer can be, for example, a brain tumor (e.g., a malignant, pre-malignant or benign brain tumor such as, for example, a glioblastoma, an astrocytoma, a meningioma, a medulloblastoma or a peripheral neuroectodermal tumor), a carcinoma (e.g., gall bladder carcinoma, bronchial carcinoma, basal cell carcinoma, adenocarcinoma, squamous cell carcinoma, small cell carcinoma, large cell undifferentiated carcinoma, adenomas, cystadenoma, etc.), a basalioma, a teratoma, a retinoblastoma, a choroidea melanoma, a seminoma, a sarcoma (e.g., Ewing sarcoma, rhabdomyosarcoma, craniopharyngeoma, osteosarcoma, chondrosarcoma, myosarcoma, liposarcoma, fibrosarcoma, leimyosarcoma, Askin's tumor, lymphosarcoma, neurosarcoma, Kaposi's sarcoma, dermatofibrosarcoma, angiosarcoma, etc.), a plasmocytoma, a head and neck tumor (e.g., oral, laryngeal, nasopharyngeal, esophageal, etc.), a liver tumor, a kidney tumor, a renal cell tumor, a squamous cell carcinoma, a uterine tumor, a bone tumor, a prostate tumor, a breast tumor including, but not limited to a breast tumor that is Her2- and/or ER- and/or PR-, a bladder tumor, a pancreatic tumor, an endometrium tumor, a squamous cell carcinoma, a stomach tumor, gliomas, a colorectal tumor, a testicular tumor, a colon tumor, a rectal tumor, an ovarian tumor, a cervical tumor, an eye tumor, a central nervous system tumor (e.g., primary CNS lymphomas, spinal axis tumors, brain stem gliomas, pituitary adenomas, etc.), a thyroid tumor, a lung tumor (e.g., non-small cell lung cancer (NSCLC) or small cell lung cancer), a leukemia or a lymphoma (e.g., cutaneous T-cell lymphomas (CTCL), non-cutaneous peripheral T-cell lymphomas, lymphomas associated with human T-cell lymphotrophic virus (HTLV) such as adult T-cell leukemia/lymphoma (ATLL), B-cell lymphoma, acute non-lymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma, etc.), a multiple myeloma, a skin tumor (e.g., basal cell carcinomas, squamous cell carcinomas, melanomas such as malignant melanomas, cutaneous melanomas or intraocular melanomas, Dermatofibrosarcoma protuberans, Merkel cell carcinoma or Kaposi's sarcoma), a gynecologic tumor (e.g., uterine sarcomas, carcinoma of the fallopian tubes, carcinoma of the endometrium, carcinoma of the cervix, carcinoma of the vagina, carcinoma of the vulva, etc.), Hodgkin's disease, a cancer of the small intestine, a cancer of the endocrine system (e.g., a cancer of the thyroid, parathyroid or adrenal glands, etc.), a mesothelioma, a cancer of the urethra, a cancer of the penis, tumors related to Gorlin's syndrome (e.g., medulloblastomas, meningioma, etc.), a tumor of unknown origin; or metastases of any thereto.

In another embodiment, the cancer is a lung tumor, a breast tumor, a colon tumor, a colorectal tumor, a head and neck tumor, a liver tumor, a prostate tumor, a glioma, glioblastoma multiforme, a ovarian tumor or a thyroid tumor; or metastases of any thereto.

In yet another embodiment, the cancer is an endometrial tumor, bladder tumor, multiple myeloma, melanoma, renal tumor, sarcoma, cervical tumor, leukemia, and neuroblastoma.

Tumors, as provided herein, may be primary tumors or metastases.

In one aspect, a pharmaceutical composition to be administered to a subject in any of the methods described herein is a catecholic butane.

In one embodiment of the methods described herein, a catecholic butane may have the structure of formula I:

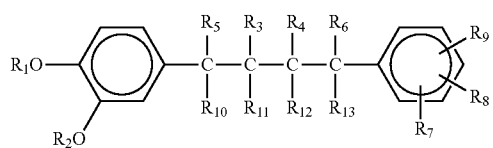

wherein $R_1$ and $R_2$ are independently H, lower alkyl, or lower acyl; $R_3$, $R_4$, $R_5$, $R_6$, $R_{10}$, $R_{11}$, $R_{12}$ and $R_{13}$ are independently H or lower alkyl; and $R_7$, $R_8$ and $R_9$ are independently H, hydroxy, lower alkoxy or lower acyloxy. Also included are pharmaceutically acceptable salts, pharmaceutically acceptable solvates, tautomers, metabolites, and prodrugs of formula I.

In another embodiment of the methods described herein, a catecholic butane may have the structure of formula I:

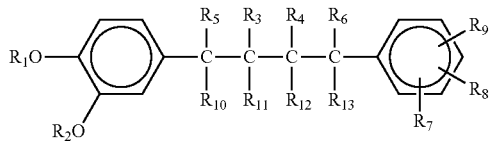

wherein $R_5$, $R_{10}$, $R_6$, and $R_{13}$ are independently H;
when $R_3$ is H, $R_{11}$ is lower alkyl; or when $R_3$ is lower alkyl, $R_{11}$ is H;
when $R_4$ is H, $R_{12}$ is lower alkyl; or when $R_4$ is lower alkyl, $R_{12}$ is H;
two of $R_7$, $R_8$, and $R_9$ are hydroxy, the other is H, and one of the hydroxy groups is in the 3-position and the other hydroxy group is in the 4-position relative to the alkylene substituent. Also included are pharmaceutically acceptable salts, pharmaceutically acceptable solvates, tautomers, metabolites, and prodrugs of formula II.

Non-limiting examples of catecholic butanes for use in the present methods include, for example, NDGA, tetra-O-methyl NDGA; tetraglycinyl NDGA; tetra-dimethylglycinyl NDGA or a salt thereof; and tri-O-methyl NDGA; nordihydroguaiaretic acid tetrapivalate; nordihydroguaiaretic acid tetrapropionate and all optical configurations thereof.

Non-limiting examples of catecholic butanes for use in the present methods also include, for example, the d-, l-, racemic mixture of d- and l-, and meso-isomers of 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl)butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; and 1-(3,4-dihydroxyphenyl)-4-(2,5-dihydroxyphenyl)butane.

In one embodiment, the catecholic butane is nordihydroguaiaretic acid (NDGA).

Pharmaceutical compositions of the present embodiments may be formulated for any route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane is formulated for oral administration. In another embodiment, the catecholic butane is formulated for intravenous administration.

By way of example only, catecholic butanes may be administered in an amount of about 5 mg/kg to about 375 mg/kg per dose; about 5 mg/kg to about 250 mg/kg per dose; about 5 mg/kg to about 200 mg/kg per dose; about 5 mg/kg to about 150 mg/kg per dose; about 5 mg/kg to about 100 mg/kg per dose; about 5 mg/kg to about 75 mg/kg per dose; or about 5 mg/kg to about 50 mg/kg per dose. Alternatively, catecholic butanes may be administered in an amount of from about 1,500 mg per day to about 2,500 mg per day; from about 1,800 mg per day to about 2,300 mg per day; or about 2,000 mg per day. In one embodiment, a catecholic butane may be contacted with target cells in a concentration in a range of about 1 µM to about 30 µM. In another embodiment, a catecholic butane may be contacted with target cells in a concentration in a range of about 1 µM to about 10 µM.

In one embodiment, a pharmaceutical composition may be administered more frequently than once every 6 days for a period of time, or more frequently than once every 2 days for a period of time. In one embodiment, a pharmaceutical composition is administered daily for four weeks. In another embodiment, a pharmaceutical composition is administered three times daily for three weeks with a one week hiatus prior to starting a new cycle. In another embodiment, a pharmaceutical composition is administered daily for one week followed by a one week hiatus. In another embodiment, a pharmaceutical composition is administered daily for two weeks followed by a two week hiatus. In another embodiment, a pharmaceutical composition is administered one time or two times daily continuously or with a one week hiatus prior to starting a new cycle. In yet another embodiment, a pharmaceutical composition is administered one time per week or two times per week.

Catecholic Butanes

As used herein, the term "catecholic butane" refers to compounds that are dual kinase inhibitors of both EGFR and IGF-1R (i.e., a single compound that is a dual kinase inhibitor).

In one embodiment, a catecholic butane may have the structure of formula I:

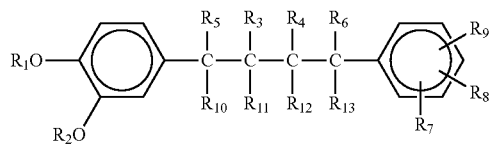

wherein $R_1$ and $R_2$ are independently H, lower alkyl, or lower acyl; $R_3$, $R_4$, $R_5$, $R_6$, $R_{10}$, $R_{11}$, $R_{12}$ and $R_{13}$ are independently H or lower alkyl; and $R_7$, $R_8$ and $R_9$ are independently H, hydroxy, lower alkoxy or lower acyloxy. Also included are pharmaceutically acceptable salts, pharmaceutically acceptable solvates, tautomers, metabolites, and prodrugs of formula I.

In another embodiment, a catecholic butane may have the structure of formula I:

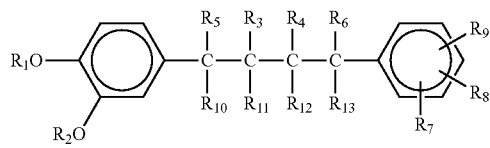

wherein $R_5$, $R_{10}$, $R_6$, and $R_{13}$ are independently H;

when $R_3$ is H, $R_{11}$ is lower alkyl; or when $R_3$ is lower alkyl, $R_{11}$ is H;

when $R_4$ is H, $R_{12}$ is lower alkyl; or when $R_4$ is lower alkyl, $R_{12}$ is H;

two of $R_7$, $R_8$, and $R_9$ are hydroxy, the other is H, and one of the hydroxy groups is in the 3-position and the other hydroxy group is in the 4-position relative to the alkylene substituent. Also included are pharmaceutically acceptable salts, pharmaceutically acceptable solvates, tautomers, metabolites, and prodrugs of formula II.

As used herein, lower alkyl is intended to generally mean $C_1$-$C_6$ alkyl, and preferably $R_3$ and $R_4$ are $C_1$-$C_3$ alkyl. As used herein, lower alkyl also represents, inter alia, methyl, ethyl, n-propyl, isopropyl, n-butyl, iso-butyl, tert-butyl, n-pentyl, isopentyl, n-hexyl, and the like.

As used herein, lower acyl is intended to generally mean [$C_1$-$C_6$] acyl, with [$C_2$-$C_6$] acyl being preferred. As used herein, lower acyl also represents groups having the general formula RCO—, e.g., acetyl ($CH_3CO$—), propionyl ($CH_3CH_2CO$—), butyryl (CH $CH_2CH_2CO$—), and the like.

Catecholic butanes may be directed to both the phenolic compounds and the conventional esters and ethers thereof. When the catecholic butane compound is, for example, a substituted phenyl, the corresponding groups are acetoxy ($CH_3CO_2$—), propionyloxy ($CH_3CH_2CO_2$—), and butyroyloxy ($CH_3CH_2CH_2CO_2$—).

Compounds may be in the form of a single optical isomer or a mixture of such isomers, e.g., a racemic mixture, or diastereoisomers.

In one embodiment, the catecholic butane is nordihydroguaiaretic acid (NDGA) or a derivative thereof. NDGA is a phenolic compound that was identified as a major component of a tea made from resinous extracts of the creosote bush *Larrea divaricatta*.

Non-limiting examples of catecholic butanes for use in the present methods include, but are not limited to, NDGA, tetra-O-methyl NDGA; tetraglycinyl NDGA; tetra-dimethylglycinyl NDGA or a salt thereof; or tri-O-methyl NDGA; nordihydroguaiaretic acid tetrapivalate; nordihydroguaiaretic acid tetrapropionate and all optical configurations thereof.

Non-limiting examples of catecholic butanes for use in the present methods also include, for example, the d-, l-, racemic mixture of d- and l-, and meso-isomers of 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3,4,5-trihydroxyphenyl)butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; and 1-(3,4-dihydroxyphenyl)-4-(2,5-dihydroxyphenyl)butane.

Other catecholic butanes described in the art are contemplated for use herein. Catecholic butanes described in, for example, U.S. Pat. Nos. 5,008,294; 6,291,524; or 6,417,234; U.S. Published Application Nos. 20080207532, 20080096967, 20060151574, 20060141029 and 20070099847 are incorporated herein by reference.

Definition of standard chemistry terms may be found in reference works, including Carey and Sundberg "Advanced Organic Chemistry 4th Ed." Vols. A (2000) and B (2001), Plenum Press, New York. Unless otherwise indicated, conventional methods of mass spectroscopy, NMR, HPLC, IR and UV/Vis spectroscopy and pharmacology, within the skill of the art are employed. Unless specific definitions are provided, the nomenclature employed in connection with, and the laboratory procedures and techniques of, analytical chemistry, synthetic organic chemistry, and medicinal and pharmaceutical chemistry described herein are those known in the art. Standard techniques can be used for chemical syntheses, chemical analyses, pharmaceutical preparation, formulation, and delivery, and treatment of patients. Reactions and purification techniques can be performed e.g., using kits of manufacturer's specifications or as commonly accomplished in the art or as described herein. The foregoing techniques and procedures can be generally performed of conventional methods well known in the art and as described in various general and more specific references that are cited and discussed throughout the present specification. Throughout the specification, groups and substituents thereof can be chosen by one skilled in the field to provide stable moieties and compounds.

The compounds presented herein may exist as tautomers. Tautomers are compounds that are interconvertible by migration of a hydrogen atom, accompanied by a switch of a single bond and adjacent double bond. In solutions where tautomerization is possible, a chemical equilibrium of the tautomers will exist. The exact ratio of the tautomers depends on several factors, including temperature, solvent, and pH. Some examples of tautomeric pairs include:

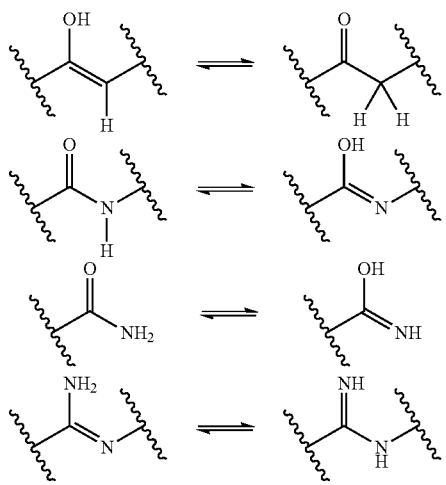

The term "pharmaceutically acceptable derivative or prodrug" as used herein, refers to any pharmaceutically acceptable salt, ester, salt of an ester or other derivative of a compound, which, upon administration to a recipient, is capable of providing (either directly or indirectly) a pharmaceutically active metabolite or residue thereof. Particularly favored derivatives or prodrugs are those that increase the bioavailability of the compounds when such compounds are administered to a patient (e.g., by allowing orally administered compound to be more readily absorbed into blood) or which enhance delivery of the parent compound to a biological compartment (e.g., the brain or lymphatic system).

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds, or by separately reacting a purified compound in its free base form with a suitable organic or inorganic acid, and isolating the salt thus formed. Examples of pharmaceutically acceptable salts include those salts prepared by reaction of the compound with a mineral or organic acid or an inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate, metaphosphate, methanesulfonate, methoxybenzoate, methylbenzoate, monohydrogen phosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate and xylenesulfonate. Other acids, such as oxalic, while not in themselves pharmaceutically acceptable, may be employed in the preparation of salts useful as intermediates in obtaining the compounds described herein and their pharmaceutically acceptable acid addition salts. See, for example, Berge et al., J. Pharm. Sci. 1977, 66, 1-19. Further, those compounds described herein which may comprise a free acid group may react with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Illustrative examples of bases include sodium hydroxide, potassium hydroxide, choline hydroxide, sodium carbonate, $N+(C1\text{-}4\text{ alkyl})_4$, and the like. Representative organic amines useful for the formation of base addition salts include ethylamine, diethylamine, ethylenediamine, ethanolamine, diethanolamine, piperazine and the like. It should be understood that compounds also include the quaternization of any basic nitrogen-containing groups they may contain. Water or oil-soluble or dispersible products may be obtained by such quaternization. See, for example, Berge et al., supra.

Catecholic butanes can also exist in various polymorphic states, all of which are herein contemplated, and which can also be useful for treating disorders. For example, polymorphs of catecholic butanes may be administered in embodiments of the methods described herein. Catecholic butanes include, for example, all crystalline forms (known as polymorphs). Polymorphs include the different crystal packing arrangements of the same elemental composition of the compound. Polymorphs can have different X-ray diffraction patterns, infrared spectra, melting points, density, hardness, crystal shape, optical and electrical properties, stability, solvates and solubility. Various factors such as the recrystallization solvent, rate of crystallization, and storage temperature can cause a single crystal form to dominate. The various polymorphs can be administered as pharmaceutical compositions.

In pharmaceutical dosage forms, active agents may be administered in the form of their pharmaceutically acceptable salts, or they may also be used alone or in appropriate association, as well as in combination, with other pharmaceutically active compounds. The following methods and excipients are merely exemplary and are in no way limiting. Methods of preparing various pharmaceutical compositions with a specific amount of active compound are known or will be apparent to those skilled in this art. For examples, see Remington's Pharmaceutical Sciences, Mack Publishing Company, Ester, Pa., 18th Edition (1990).

The pharmaceutically acceptable excipients, such as vehicles, adjuvants, carriers or diluents, are conventional in the art. Suitable excipient vehicles are, for example, water, saline, dextrose, glycerol, ethanol, or the like, and combinations thereof. In addition, if desired, the vehicle may contain minor amounts of auxiliary substances such as pH adjusting and buffering agents, tonicity adjusting agents, stabilizers, wetting agents or emulsifying agents. Actual methods of preparing such dosage forms are known, or will be apparent, to those skilled in the art. See, e.g., Remington's Pharmaceutical Sciences, Mack Publishing Company, Easton, Pa., 17th edition, 1985. The composition or formulation to be administered will, in any event, contain a quantity of the agent adequate to achieve the desired state in the subject being treated.

The active agents can be formulated into preparations for injection by dissolving, suspending or emulsifying them in an aqueous or non-aqueous solvent, such as vegetable or other similar oils, including corn oil, castor oil, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents can be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose, saccharin or aspartame.

Pharmaceutical preparations can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. The formulations can be presented in unit-dose or multi-dose containers, for example sealed ampoules and vials, and can be stored in powder form or in a freeze-dried (lyophilized) condition requiring only the addition of the sterile liquid carrier, for example, saline or sterile pyrogen-free water, immediately prior to use. Extemporaneous injection solutions and suspensions can be prepared from sterile powders, granules and tablets of the kind previously described.

Formulations for parenteral administration include aqueous and non-aqueous (oily) sterile injection solutions of the active compounds which can contain antioxidants, buffers, biocide, bacteriostats and solutes which render the formulation isotonic with the blood of the intended recipient; and aqueous and non-aqueous sterile suspensions which can include suspending agents and thickening agents. Examples of suitable isotonic vehicles for use in such formulations include Sodium Chloride Injection, Ringer's Solution, or Lactated Ringer's Injection. Suitable lipophilic solvents or vehicles include fatty oils such as sesame oil, or synthetic fatty acid esters, such as ethyl oleate or triglycerides, or liposomes or other microparticulate systems can be used to target the compound to blood components or one or more organs. The concentration of the active ingredient in the solution can vary widely. Typically, the concentration of the active ingredient in the solution is from about 1 ng/ml to about 10 µg/ml, for example from about 10 ng/ml to about 1 µg/ml. Aqueous injection suspensions can contain substances which increase the viscosity of the suspension, such as sodium carboxymethyl cellulose, sorbitol, or dextran. Optionally, the suspension can also contain suitable stabilizers or agents which increase the solubility of the compounds to allow for the preparation of highly concentrated solutions Pharmaceutical preparations can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions can take the form of tablets, lozenges, pastilles, or gels formulated in conventional manner. Such compositions can comprise the active ingredient in a flavored basis such as sucrose and acacia or tragacanth.

Pharmaceutical preparations can be administered topically, that is by non-systemic administration. This includes the application of the compositions externally to the epidermis or the buccal cavity and the instillation of such compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, suspensions, powders, solutions, spray, aerosol, oil, and drops suitable for administration to the eye, ear or nose. Alternatively, a formulation can comprise a patch or a dressing such as a bandage or adhesive plaster impregnated with active ingredients and optionally one or more excipients or diluents. The amount of active ingredient present in the topical formulation can vary widely. The active ingredient can comprise, for topical administration, from 0.001% to 10% w/w, for instance from 1% to 2% by weight of the formulation. It can however comprise as much as 10% w/w but preferably will comprise less than 5% w/w, more preferably from 0.1% to 1% w/w of the formulation.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

The active agents can be utilized in aerosol formulation to be administered via inhalation.

The compounds of the present embodiments may be formulated into pressurized acceptable propellants such as dichlorodifluoromethane, propane, nitrogen and the like.

Furthermore, the active agents can be made into suppositories by mixing with a variety of bases such as emulsifying bases or water-soluble bases. The compounds of the present embodiments may be administered rectally via a suppository. The suppository can include vehicles such as cocoa butter, carbowaxes and polyethylene glycols, which melt at body temperature, yet are solidified at room temperature.

For oral preparations, the active agents can be used alone or in combination with appropriate additives to make tablets, powders, granules or capsules with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. For oral rinses, the preparations can be made in a manner conventional in the art.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

Some catecholic butanes are water-soluble, hydrophilic compounds. Some embodiments include formulation of hydrophilic compounds in a pharmaceutically acceptable carrier or excipient and delivery of such as oral formulations, such as in the form of an aqueous liquid solution of the compound, or the compounds can be lyophilized and delivered as a powder, made into a tablet, or the compounds can be encapsulated.

The tablets herein can be enteric coated tablets. The formulations herein can be sustained release, either slow release or rapid release formulations.

The amount of the catecholic butanes be included in the oral formulations can be adjusted depending on the desired dose to be administered to a subject. Such an adjustment is within the skill of persons conventional in the art.

Some catecholic butanes are hydrophobic or lipophilic compounds. The absorption of lipophilic compounds in the gut can be improved by using pharmaceutically acceptable carriers that can enhance the rate or extent of solubilization of the compound into the aqueous intestinal fluid. Lipidic carriers are known in the art. The formulations herein can be delivered as oral liquids or can be encapsulated into various types of capsules.

The present embodiments include, in one example, a formulation containing lipophilic catecholic butanes that are formulated for oral delivery by dissolution of such compounds in triacylglycerols, and the formulation is then encapsulated for oral delivery. Triacyglycerols are molecules with long chain and/or medium chain fatty acids linked to a glycerol molecule. The long chain fatty acids range from about $C_{14}$ to $C_{24}$, and can be found in common fat. The medium chain fatty acids range from about $C_6$ to $C_{12}$, and can be found in coconut oil or palm kernel oil. Triacylglycerols suitable for use herein include structured lipids that contain mixtures of either short-chain or medium chain fatty acids or both, esterified on the same glycerol molecule.

In another embodiment, one or more surfactants can be added to a mixture of catecholic butanes and lipidic carrier such that the drug is present in fine droplets of oil/surfactant mix. The surfactants can act to disperse the oily formulation on dilution in the gastrointestinal fluid.

The present embodiments also include a formulation for oral delivery of the catecholic butanes in the form of a microemulsion consisting of hydrophilic surfactant and oil. The micro-emulsion particles can be surfactant micelles containing solubilized oil and drug.

Formulations suitable for oral administration can be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient can also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets can be made by compression or molding, optionally with one or more accessory ingredients. Compressed tablets can be prepared by compressing in a suitable machine the active ingredient in a free-flowing form such as a powder or granules, optionally mixed with binders (e.g., povidone, gelatin, hydroxypropylmethyl cellulose), inert diluents, preservative, disintegrant (e.g., sodium starch glycolate, cross-linked povidone, cross-linked sodium carboxymethyl cellulose) or lubricating, surface active or dispersing agents. Molded tablets can be made by molding in a suitable machine a mixture of the powdered compound moistened with an inert liquid diluent. The tablets can optionally be coated or scored and can be formulated so as to provide slow or controlled release of the active ingredient therein. Tablets can optionally be provided with an enteric coating, to provide release in parts of the gut other than the stomach. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or Dragee coatings for identification or to characterize different combinations of active compound doses.

Also suitable for oral administration are formulations of the catecholic butanes in a solid lipid nanoparticle preparation. Solid lipid nanoparticles can be prepared in any manner conventional in the art.

In one embodiment, the solid lipid nanoparticle can be prepared in a hot homogenization process by homogenization of melted lipids at elevated temperature. In this process, the solid lipid is melted and the catecholic butan, is dissolved in the melted lipid. A pre-heated dispersion medium is then mixed with the drug-loaded lipid melt, and the combination is mixed with a homogenisator to form a coarse pre-emulsion.

High pressure homogenization is then performed at a temperature above the lipids melting point to produce a oil/water-nanoemulsion. The nanoemulsion is cooled down to room temperature to form solid lipid nanoparticles.

In another embodiment, the solid lipid nanoparticles can be prepared in a cold homogenization process. In this process, the lipid is melted and the catecholic butane is dissolved in the melted lipid. The drug-loaded lipid is then solidified in liquid nitrogen or dry ice. The solid drug-lipid is ground in a powder mill to form 50-100 µm particles. The lipid particles are then dispersed in cold aqueous dispersion medium and homogenized at room temperature or below to form solid lipid nanoparticles.

Also provided herein, in one example, is a formulation of the lipophilic catecholic butanes in liposomes or micelles for oral delivery. These formulations can be made in any manner conventional in the art. Micelles are typically lipid monolayer vesicles in which the hydrophobic drug associates with the hydrophobic regions on the monolayer. Liposomes are typically phospholipids bilayer vesicles. A lipophilic catecholic butane will typically reside in the center of these vesicles.

Also provided herein, in another example, is a formulation of the catecholic butanes for intravenous administration. Catecholic butanes may be formulated for injection into animals with a pharmaceutically acceptable carrier. Carriers include, but are not limited to one or more solubilizing agents and/or an excipient such as, for example: (a) a water-soluble organic solvent other than dimethyl sulfoxide; provided that when the water-soluble organic solvent is propylene glycol, the propylene glycol is in the absence of white petrolatum, in the absence of xanthan gum (also known as xantham gum and xantham gum) and in the absence of at least one of glycerine or glycine, when the water-soluble organic solvent is polyethylene glycol, the polyethylene glycol is present in the absence of ascorbic acid or butylated hydroxytoluene ("BHT"), and when the polyethylene glycol is polyethylene glycol 400, the polyethylene glycol 400 is present in the absence of polyethylene glycol 8000; (b) a cyclodextrin; (c) an ionic, non-ionic or amphipathic surfactant, provided that when the surfactant is a non-ionic surfactant, the non-ionic surfactant is present in the absence of xanthan gum; (d) a modified cellulose; (e) a water-insoluble lipid other than castor oil; or a combination of any of the carriers (a)-(e).

Pharmaceutical compositions can be in the form of a sterile injectable aqueous solution. Among the acceptable vehicles and solvents that can be employed are water, Ringer's solution and isotonic sodium chloride solution. The sterile injectable preparation can also be a sterile injectable oil-in-water microemulsion where the active ingredient is dissolved in the oily phase. For example, the active ingredient can be first dissolved in a mixture of soybean oil and lecithin. The oil solution then introduced into a water and glycerol mixture and processed to form a microemulsion. The injectable solutions or microemulsions can be introduced into a patient's blood-stream by local bolus injection. Alternatively, it can be advantageous to administer the solution or microemulsion in such a way as to maintain a constant circulating concentration of the instant compound. In order to maintain such a constant concentration, a continuous intravenous delivery device can be utilized. An example of such a device is the Deltec CADD-PLUS™ model 5400 intravenous pump. The pharmaceutical compositions can be in the form of a sterile injectable aqueous or oleaginous suspension for intramuscular and subcutaneous administration. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example as a solution in 1,3-butanediol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Also provided herein is a formulation of the catecholic butanes for intra-arterial administration, with or without accompanying blood brain barrier disruption ("BBBD"), and with or without occlusion, such as in hepatic artery chemoembolization. Briefly, where catecholic butanes are administered intra-arterially with occlusion, primary arteries leading to the target site are catheterized and the catecholic butanes may be applied through a catheter. Embolization of the arteries, in order to retain the catecholic butanes at the target site for a longer period, may be performed using polyvinyl alcohol particles alone or in combination with coils. Intra-arterial delivery of the catecholic butanes may include water soluble compositions. The drugs or agents herein may be dissolved in saline prior to intra-arterial injection and such injection may be preceded by heparin treatment and sedation.

Osmotic disruption of the blood brain barrier ("BBB") as conventional in the art may accompany intra-arterial delivery of the agents herein. Such a procedure can be used to increase the transfer of drugs into the central nervous system ("CNS") preferably just prior to intra-arterial delivery. For such disruption, a catheter is placed into an artery, usually the superficial temporal artery, leading to the brain and the BBB is disrupted with a solution of mannitol. This invasive procedure is typically performed while the patient is under general anesthesia. Such treatment may require prior hydration and administration of anticonvulsants and/or atropine.

Also provided herein, in one example, is a formulation of catecholic butanes for intranasal delivery and intranasal delivery thereof. Intranasal delivery may advantageously build up a higher concentration of the active agents in the brain than can be achieved by intravenous administration. Also, this mode of delivery avoids the problem of first pass metabolism in the liver and gut of the subject receiving the drug.

The amount of the active agents that can be absorbed partly depends on the solubility of the drug in the mucus, a composition that consists of about 95% water solution of serum proteins, glycoproteins, lipids and electrolytes. Generally, as lipophilicity of the active agents herein increases, the drug concentration in the CSF also increases.

Hydrophilic catecholic butanes may be dissolved in a pharmaceutically acceptable carrier such as saline, phosphate buffer, or phosphate buffered saline. In one embodiment, a 0.05 M phosphate buffer at pH 7.4 can be used as the carrier.

Intranasal delivery of the present agents may be optimized by adjusting the position of the subject when administering the agents. For example, the head of the patient may be variously positioned upright-90°, supine-90°, supine-45°, or supine-70° to obtain maximal effect.

The carrier of the composition of catecholic butanes may be any material that is pharmaceutically acceptable and compatible with the active agents of the composition. Where the carrier is a liquid, it can be hypotonic or isotonic with nasal fluids and within the pH of about 4.5 to about 7.5. Where the carrier is in powdered form it is also within an acceptable pH range.

The carrier composition for intranasal delivery may optionally contain lipophilic substances that may enhance absorption of the active agents across the nasal membrane and into the brain via the olfactory neural pathway. Examples of such lipophilic substances include, but are not limited to, gangliosides and phosphatidylserine. One or several lipophilic adjuvants may be included in the composition, such as, in the form of micelles.

The pharmaceutical composition of active agents for intranasal delivery to a subject for treatment of the diseases, disorders, or conditions herein can be formulated in the manner conventional in the art as described in, for example, U.S. Pat. No. 6,180,603 which is incorporated herein by reference. For example, the composition herein can be formulated as a powder, granules, solution, aerosol, drops, nanoparticles, or liposomes. In addition to the active agents, the composition may contain appropriate adjuvants, buffers, preservatives, salts. Solutions such as nose drops may contain anti-oxidants, buffers, and the like.

Catecholic butanes may be delivered to a subject for treatment by surgical implantation into a desired site, such as by implantation of a biodegradable polymer containing the catecholic butane.

Thus, the biodegradable polymer herein can be any polymer or copolymer that would dissolve in the interstitial fluid, without any toxicity or adverse effect on host tissues. Preferably, the polymer or monomers from which the polymer is synthesized is approved by the Food and Drug Administration for administration into humans. A copolymer having monomers of different dissolution properties is preferred so as to control the dynamics of degradation, such as increasing the proportion of one monomer over the other to control rate of dissolution.

In one embodiment, the polymer is a copolymer of 1,3-bis-(p-carboxyphenoxy)propane and sebacic acid [p(CPP: SA)], as described in Fleming A. B. and Saltzman, W. M., Pharmacokinetics of the Carmustine Implant, Clin. Pharmacokinet, 41: 403-419 (2002); and Brem, H. and Gabikian, P. (2001). In another embodiment, the polymer is a copolymer of polyethylene glycol ("PEG") and sebacic acid, as described in Fu, J. et al., (2002) Biomaterials, 23: 4425-4433.

Polymer delivery systems are applicable to delivery of both hydrophobic and hydrophilic catecholic butanes described herein. The catecholic butanes may be combined with the biodegradable polymers and surgically implanted at the desired or affected site. Some polymer compositions are also usable for intravenous or inhalation therapy herein.

Catecholic butanes may be delivered systemically and/or locally by administration to the lungs through inhalation Inhalation delivery of drugs has been well accepted as a method of achieving high drug concentration in the pulmonary tissues without triggering substantial systemic toxicity, as well as a method of accomplishing systemic circulation of the drug. The techniques for producing such formulations are conventional in the art. Efficacy against pulmonary diseases may be seen with either hydrophobic or hydrophilic catecholic butanes delivered in this manner.

For pulmonary delivery via inhalation, catecholic butanes may be formulated into dry powders, aqueous solutions, liposomes, nanoparticles, or polymers and administered, for example, as aerosols. Hydrophilic formulations may also be taken up through the alveolar surfaces and into the bloodstream for systemic applications.

In one embodiment, the polymers containing the active agents herein are made and used as described in Fu, J. et al. (2002) supra. For example, the polymers herein can be polymers of sebacic acid and polyethylene glycol ("PEG"), or can be poly(lactic-co-glycolic) acid ("PLGA"), or polymers of polyethyleneimine ("PEI") and poly-L-lysine ("PLL").

In another embodiment, catecholic butanes for inhalation delivery may be dissolved in saline or ethanol before nebulization and administered.

In a further embodiment, the agents herein are also effective when delivered as a dry powder, prepared in the manner conventional in the art.

In one embodiment, delivery of the NDGA compounds may be accomplished with the aid of microprocessors embedded into drug delivery devices, such as, for example, Smart-Mist™ and AERx™.

The appropriate dose to be administered depends on the subject to be treated, such as the general health of the subject, the age of the subject, the state of the disease or condition, the weight of the subject, the size of the tumor, for example.

Pharmaceutical compositions may be formulated for a route of administration such as, for example, intranasal administration; oral administration; inhalation administration; subcutaneous administration; transdermal administration; intra-arterial administration, with or without occlusion; intracranial administration; intraventricular administration; intravenous administration; buccal administration; intraperitoneal administration; intraocular administration; intramuscular administration; implantation administration; and central venous administration. In one embodiment, the catecholic butane is formulated for oral administration. In another embodiment, the catecholic butane is formulated for intravenous administration.

An active agent may be administered in a single or, more typically, multiple doses. Preferred dosages for a given agent are readily determinable by those of skill in the art by a variety of means. Other effective dosages can be readily determined by one of ordinary skill in the art through routine trials establishing dose response curves. The amount of agent will, of course, vary depending upon the particular agent used.

The frequency of administration of the active agent, as with the doses, will be determined by the care giver based on age, weight, disease status, health status and patient responsiveness. Thus, the agents may be administered one or more times daily, weekly, monthly or as appropriate as conventionally determined. The agents may be administered intermittently, such as for a period of days, weeks or months, then not again until some time has passed, such as 3 or 6 months, and then administered again for a period of days, weeks, or months.

Unit dosage forms for injection or intravenous administration may comprise the API in a composition as a solution in sterile water, normal saline or another pharmaceutically acceptable carrier.

Methods of Treatment

The present methods target an unmet need for NSCLC patients. The present application discloses small molecule, kinase inhibitors that inhibit multiple signaling pathways central to tumor growth. NDGA (TT-100) is uniquely positioned to address unmet need in lung cancer because there are no approved therapies.

Activating Mutations of EGFR drive approximately 10+% or more of all NSCLC. Tarceva/Iressa are effective against these tumors initially; however, tumors develop resistance in 3-12 months via 2 primary mechanisms: (1) mutation—approximately 50+% or more develop ATP binding site mutations (T790M); and (2) enhanced signaling through alternative pathways: (a) cMet (which enhances tumor survival) and/or (b) IGF1R (which enhances tumor growth signaling).

Figure 4:
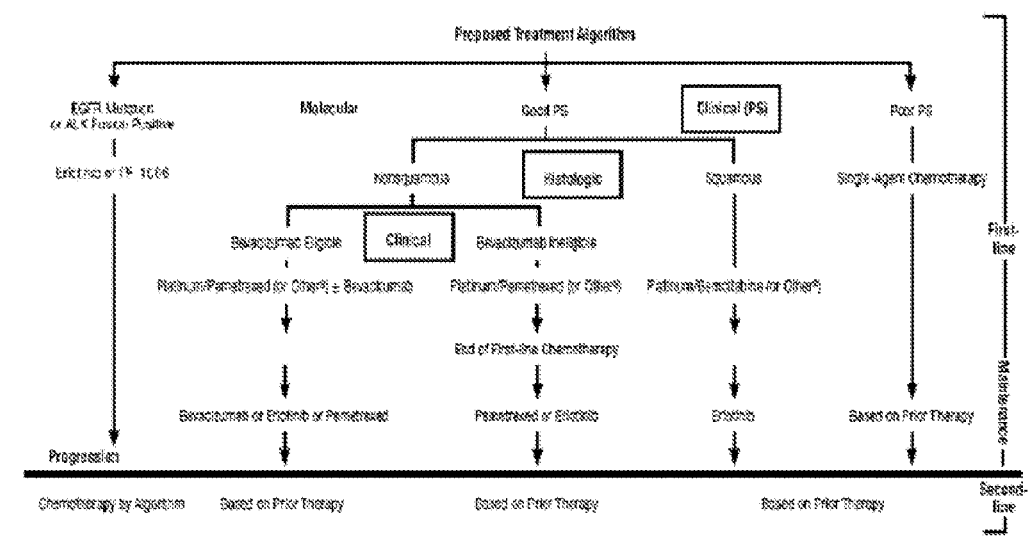
FIG. 4 Illustrates an exemplary proposed treatment algorithm chart.

There are no approved/effective therapies=4-6 month survival. FIG. 4 provides an exemplary proposed treatment algorithm chart.

NDGA (TT-100) is a small molecule (MW 302) with potential as an effective cancer therapy. It provides a competitive advantage over previously described compounds in that the present inventors have identified a novel proposed mechanism of action (MOA), which has been market validated (EGFR & cMet) and clinically validated (IGFR). NDGA binds to a new binding site determined by the present inventors and has broad activity (in vitro and in 10 xenograft models). Phase 1b and 2a clinical data have determined that the compound is safe and well tolerated. Dose selection has also been determined.

Figure 5:
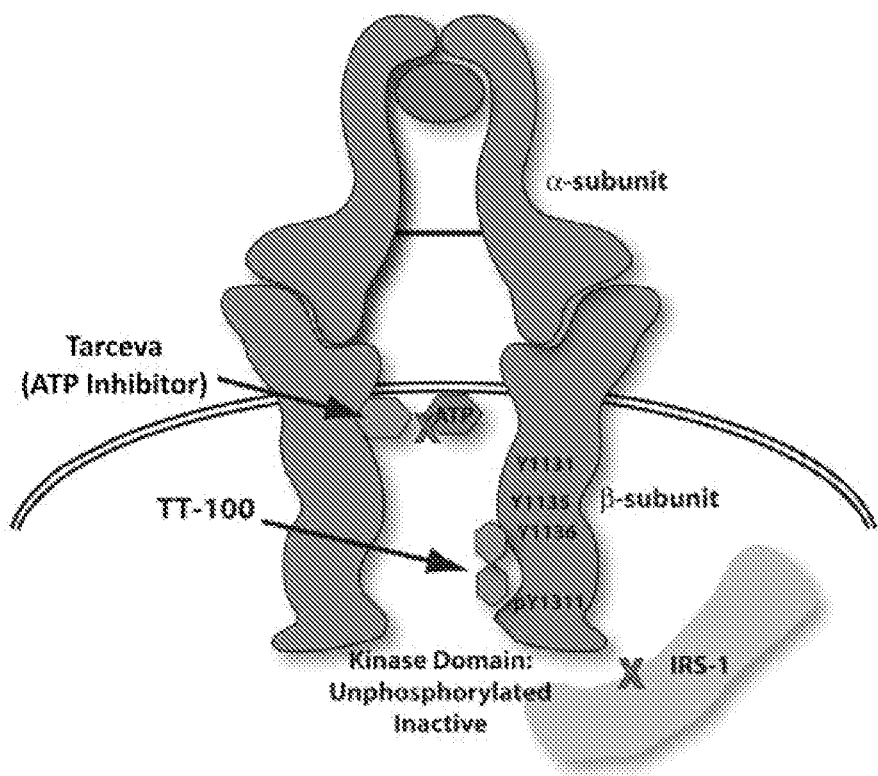
FIG. 5. Provides a cartoon illustration of the substrate-binding domain of IGF-1R. Tarceva®/Iressa® bind at the ATP binding domain. In contrast, NDGA (TT-100) binds at the substrate-binding domain.

The present inventors have identified that a novel binding site circumvents the primary driver of resistance for a variety of chemotherapeutic and small molecule cancer agents. A T790m mutation occurs at ATP binding domain. Tarceva®/Iressa® bind at the ATP binding domain. In contrast, NDGA (TT-100) binds at the substrate-binding domain as illustrated in FIG. 5.

Figure 9:
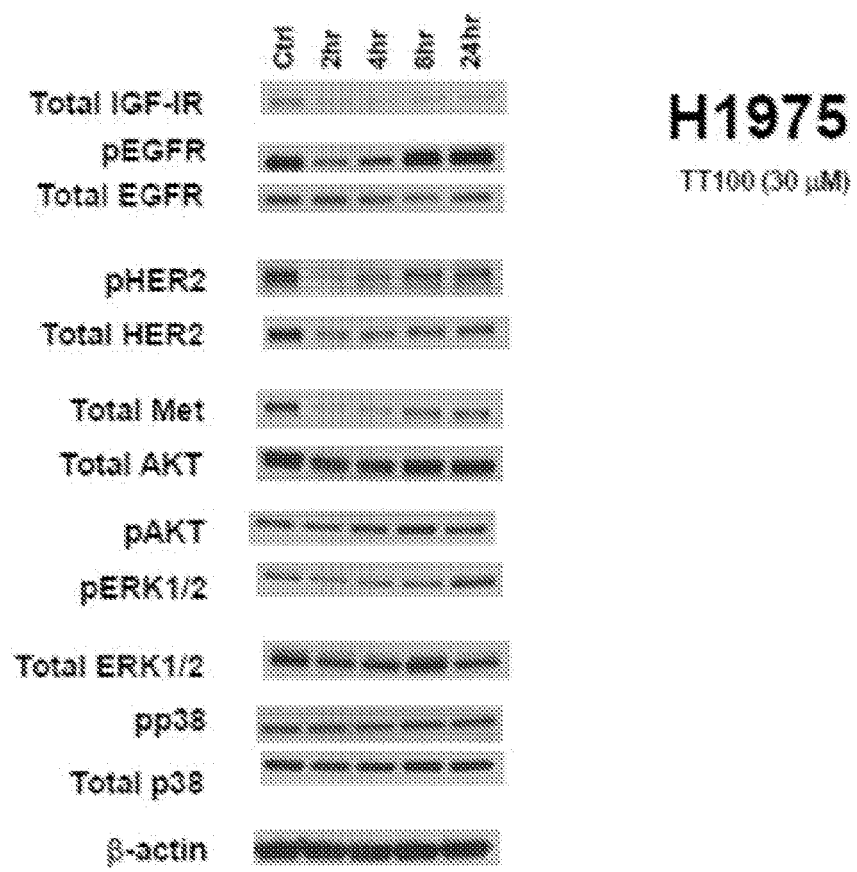
FIG. 9. NDGA inhibits multiple kinases in overlapping pathways: IGF-IR, EGFR, HER2, and Met show reduction in total protein levels over time-course following treatment at 2, 4, 8 and 24 hours compared to control.

NDGA (TT-100) binds to a site distinct from ATP pocket.

tein levels over time-course (2, 4, 8 and 24 hours) following treatment compared to control beta actin as illustrated in FIG. 9.

Figure 10:
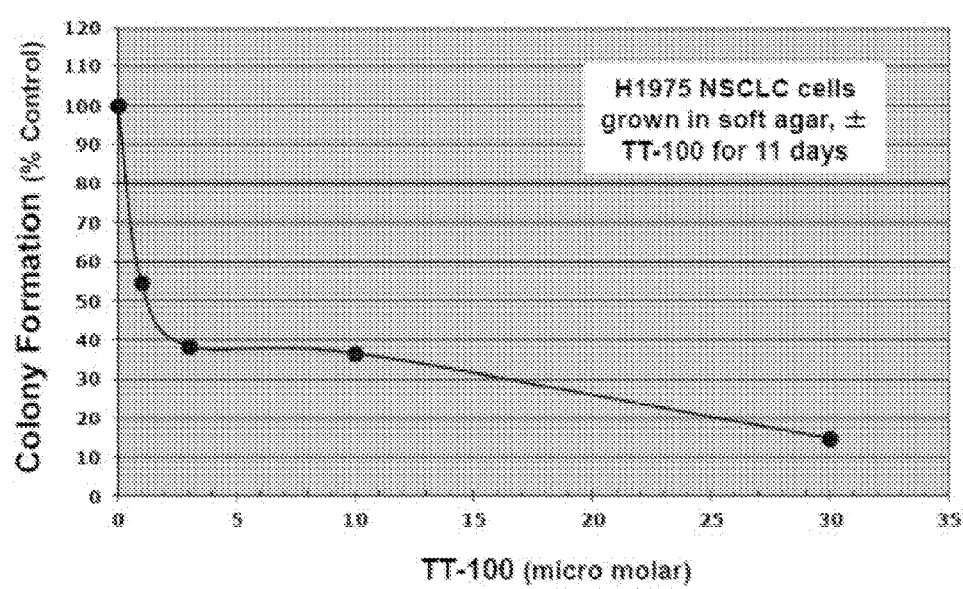
FIG. 10. H1975 NSCLC cells were grown in soft agar with and without NDGA for 11 days. Colony formation was determined and results reported normalized to control values as illustrated in FIG. 10.

H1975 NSCLC cells were grown in soft agar with and without NDGA for 11 days. Colony formation was determined and results reported normalized to control values as illustrated in FIG. 10. NDGA (TT-100) was determined to be active vs. Iressa®-resistant NSCLC cells (T790M).

NSCLC cell lines tested in these experiments are as follows in Table 1:

| Cell Line | KRAS | p53 | STK11 (LKB1) | BRAF | PTEN | RB | PI3K | EGFR | CDKN2a (p16) | SMARCA4 (BRG1) | CTNNB1 (b-Catenin) | Histology |
|---|---|---|---|---|---|---|---|---|---|---|---|---|
| *A549* | *G12S* | *wt* | *mt/hom* | *wt* | *wt* | *wt* | *wt* | *wt* | *mt/hom* | *mt/hom* | *wt* | *lung carcinoma* |
| *Calu-1* | *G12C* | *wt* | *wt* | *wt* | *wt* | *wt* | *wt* | *wt* | *wt* | *wt* | *wt* | *lung carcinoma* |
| *A427* | *G12D* | *wt* | *mt/hom* | *wt* | *wt* | *wt* | *wt* | *wt* | *mt/hom* | *mt/hom* | *mt/hom* | *lung carcinoma* |
| *H460* | *Q61H* | *wt* | *mt/hom* | *wt* | *wt* | *wt* | *mt/het* | *wt* | *mt/hom* | *wt* | *wt* | *large cell* |
| HCC827 | wt | | | | | | wt | mt/het | | | | lung adenocarcinoma |
| H1975 | wt | mt/hom | wt | wt | wt | wt | mt/het | mt/het | mt/hom | wt | wt | lung adenocarcinoma |
| H1650 | wt | mt/hom | wt | wt | wt (Null) | wt | wt | mt/het | mt/hom | wt | wt | lung BAC |
| H1666 | wt | wt | mt/het | mt/het | wt | wt | wt | wt | mt/hom | wt | wt | lungBAC |
| *H358* | *G12C* | *wt/ (null)* | *wt* | *wt* | *wt* | *wt* | *wt* | *wt* | *wt* | *wt* | *wt* | *lung BAC* |
| *H727* | *G12V* | *mt/hom* | *wt* | *wt* | *wt* | *wt* | *wt* | *wt* | *wt* | *wt* | *wt* | *lung carcinoidendocrine tumor* |
| *H1355* | *G13C* | *mt/hom* | *mt/hom* | *wt* | *wt* | *wt* | *wt* | *wt* | *wt* | *wt* | *wt* | *lung carcinoma* |

EGFR mutations are shown in bold font; KRAS mutations are shown in italicized font; and EGFR/KRAS wt is indicated by bold underlining.
*The data was obtained from the Wellcome Trust Sanger Institute Cancer Genome Project web site, sanger.ac.uk/genetics/CGP.
HCC827 and H1650 have deletions of exon 19 of the EGFR, which is an activating mutation. H1975 has an activating mutation (L858R, along with a Tarceva resistance mutation, T790M.

Figure 2:
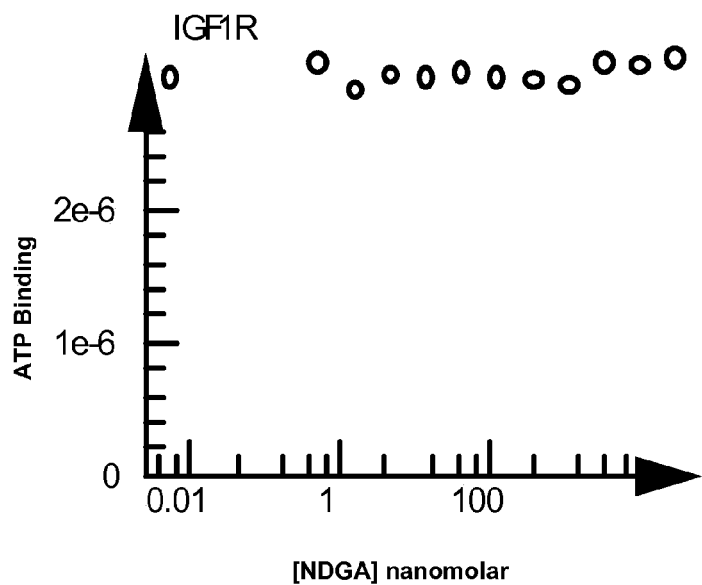
FIG. 2. NDGA does not interfere with binding of a labeled ATP analog to recombinant IGF-1R at concentrations shown to inhibit IGF-1R kinase activity, or any concentration of NDGA up to 100 µM.

A non-ATP competitive mechanism of action was demonstrated by an ATP binding competition assay. Radiolabelled ATP was bound to purified IGF-1R prior to incubation with NDGA (TT-100). Increasing concentrations of NDGA do not compete off ATP binding to IGF-1R kinase domain. The amount of ATP bound to IGF-1R unchanged at 30 μM NDGA as illustrated in FIG. 2.

Figure 6:
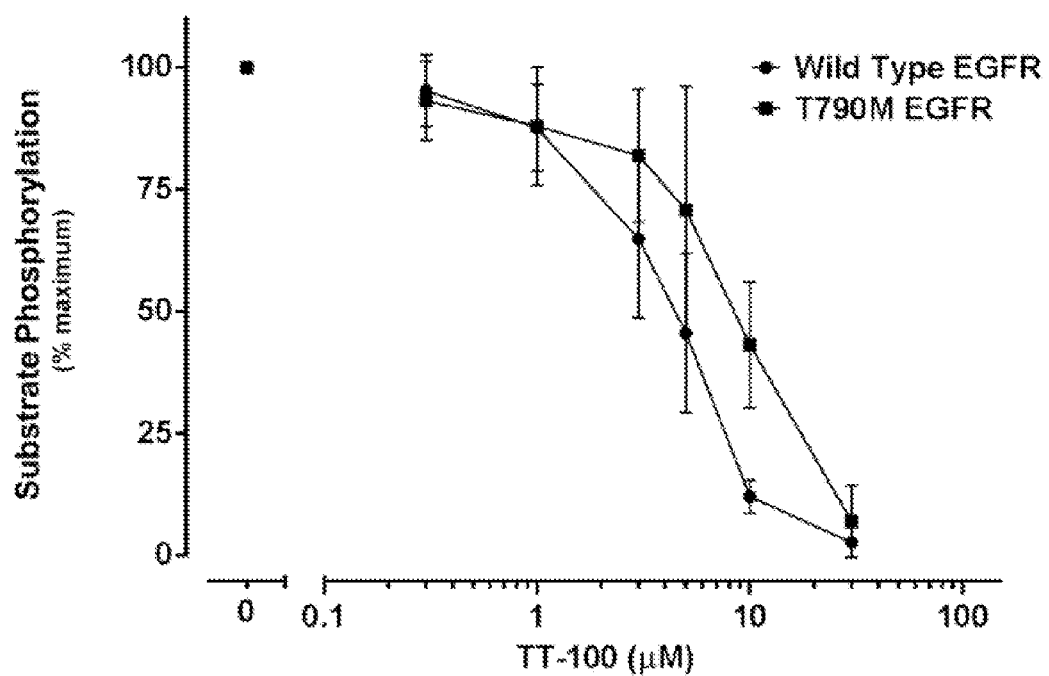
FIG. 6. NDGA (TT-100) inhibits substrate phosphorylation EGFR.

NDGA (TT-100) inhibits substrate phosphorylation EGFR as illustrated in FIG. 6.

NDGA inhibits multiple pathways central to NSCLC growth/metastasis. NDGA inhibits a range of receptor tyrosine kinases (RTKs) in overlapping pathways. Data from 3 sources show inhibition of multiple oncogenic kinases: cMet, KDR (VEGFR2), EGFR, and IGF1R by NDGA. The inhibition of these targets appears to be via a mechanism of action that is distinct from approved tyrosine kinase inhibitors (TKIs).

Figure 7:
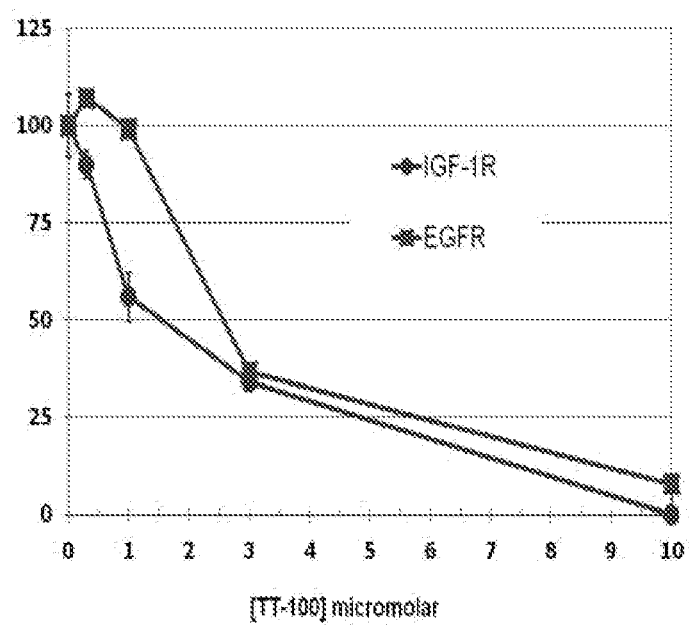
FIG. 7. NDGA (TT-100) inhibits kinase central to Tarceva® resistance. TT-100 inhibits IGF1R (circles) and EGFR (squares) with an IC50 of 1-3 mm.

NDGA (TT-100) inhibits kinase central to Tarceva® resistance. TT-100 inhibits IGF1R and EGFR with an IC50 of 1-3 mm as illustrated in FIG. 7.

Figure 8:
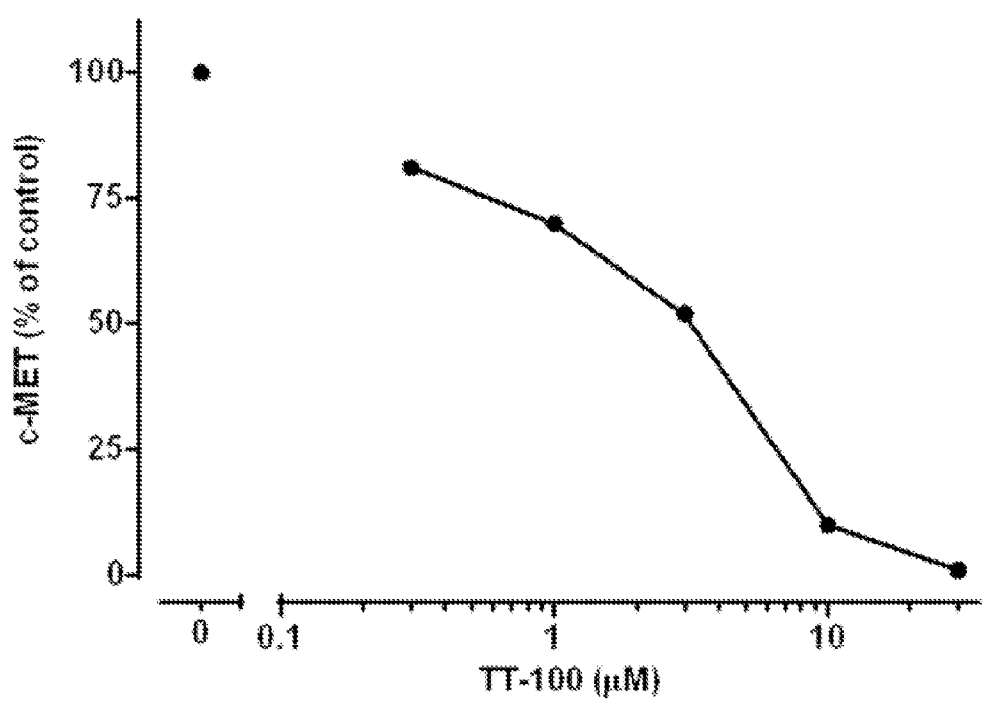
FIG. 8. TT-100 inhibits c-met with an IC50 of 3 mm.

TT-100 inhibits c-met with an IC50 of 3 mm as illustrated in FIG. 8.

Figure 11:
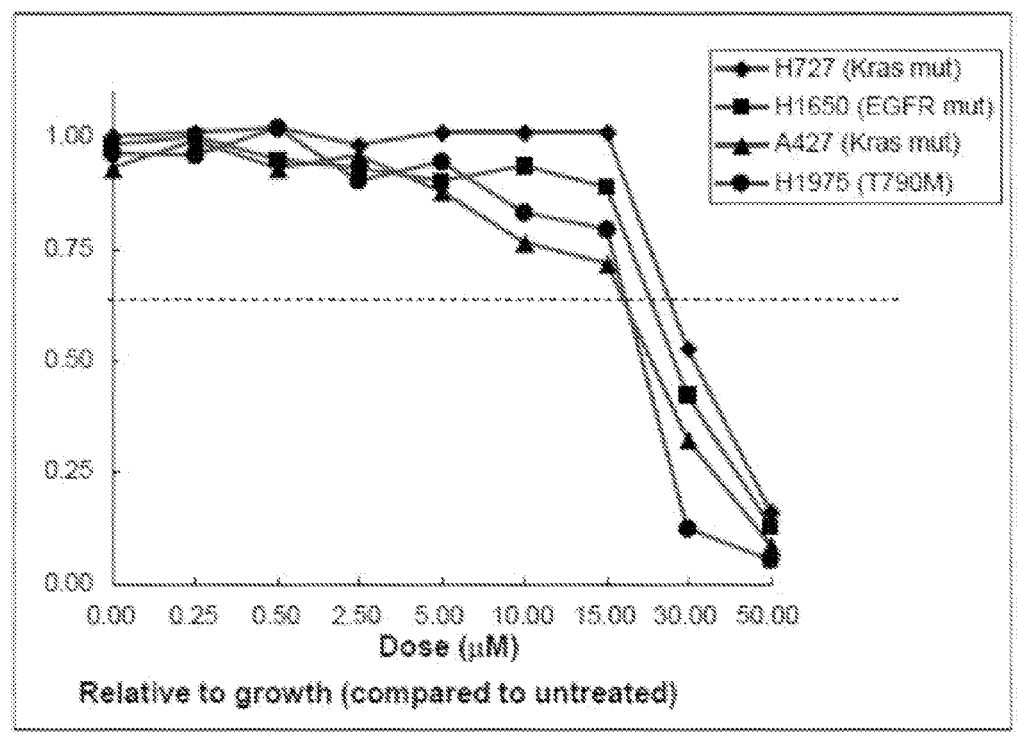
FIG. 11. Data illustrating that Tarceva® resistant cell lines are sensitive to NDGA comparing Kras mutants, EGFR mutants, and a T790M mutation. Dose of NDGA is shown on the x axis. Growth is shown on the y axis compared to untreated cells. A description of the mutations in the cell lines are identified below in Table 1.

NDGA inhibits multiple kinases in overlapping pathways: IGF-IR, EGFR, HER2, and Met show reduction in total pro- Data illustrating that Tarceva® resistant cell lines are sensitive to NDGA as shown in FIG. 11.

Figure 12:
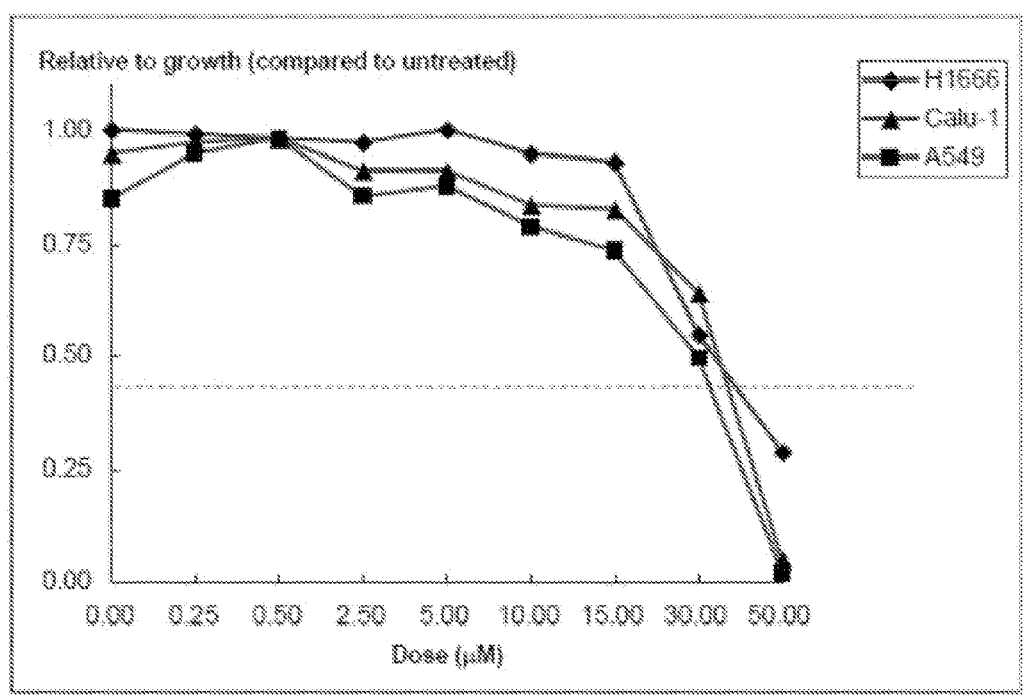
FIG. 12. Additional NSCLC cell lines were also shown to be sensitive to NDGA. Dose of NDGA is shown on the x axis. Growth is shown on the y axis compared to untreated cells.

Additional NSCLC cell lines were also shown to be sensitive to NDGA as shown in FIG. 12.

Synergy of NDGA (≥15 mM), with Tarceva® (erlotinib) was demonstrated in 9 out of 11 NSCLC cell lines. Each cell line is listed at an effective dose of 25%, 50%, and 75%

TABLE 2

| Cell Line | ED25 | ED50 | ED75 |
|---|---|---|---|
| HCC827 | 6.879* | 2.619* | 1.005 |
| H1355 | <u>0.607+</u> | <u>0.153+</u> | <u>0.053+</u> |
| H460 | <u>0.707+</u> | <u>0.605+</u> | <u>0.555+</u> |
| H358 | 0.998 | *1.156** | *1.425** |
| H1666 | *13.01** | *2.491** | <u>0.565+</u> |
| Calu-1 | *1.108** | <u>0.803+</u> | <u>0.583+</u> |
| A549 | 1.032 | <u>0.784+</u> | <u>0.599+</u> |
| H727 | *1.218** | <u>0.857+</u> | <u>0.668+</u> |
| H1650 | <u>0.942+</u> | *1.294** | *1.858** |
| A427 | 1.045 | <u>0.812+</u> | <u>0.632+</u> |
| H1975 | *1.264 | 1.020** | <u>0.881+</u> |

Non-additive effects are shown in italics with an asterisk. Additive effects are shown in bold text. Synergistic effects are shown in underlined text with a "+" symbol.

CI (combination index) plots of NDGA (TT-100) in combination with erlotinib were generated. The plots are used to quantitatively depict synergism (CI<1), additivity (CI=1), or antagonism (CI>1). The dotted line depicts the CI value of 1. These plots were generated from the data obtained from the combination dose effect curves using the Calcusyn software.

Figure 13:
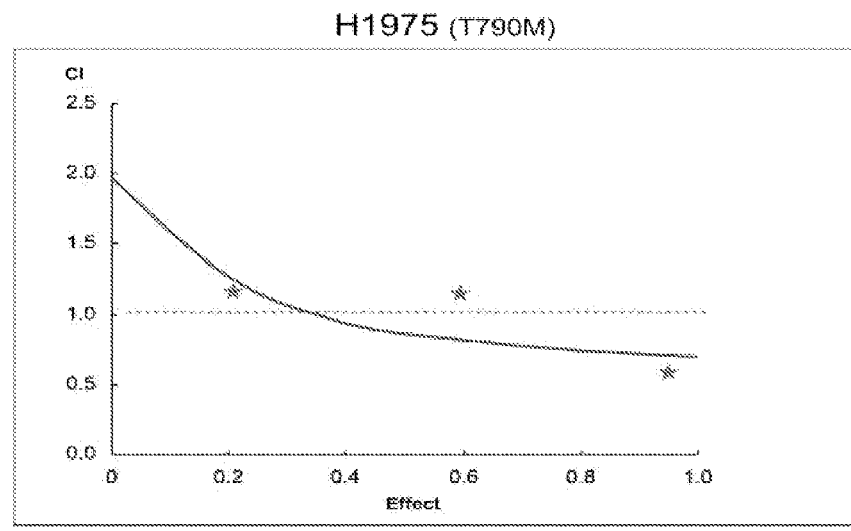
FIGS. 13A-B. CI (combination index) plots of NDGA (TT-100) in combination with erlotinib. The plots are used to quantitatively depict synergism (CI<1), additivity (CI=1), or antagonism (CI>1). The dotted line depicts the CI value of 1. A combination of NDGA and Tarceva® demonstrated synergy in a T790M cell line. These plots were generated from the data obtained from the combination dose effect curves using the Calcusyn software (FIG. 13A).
Figure 13:
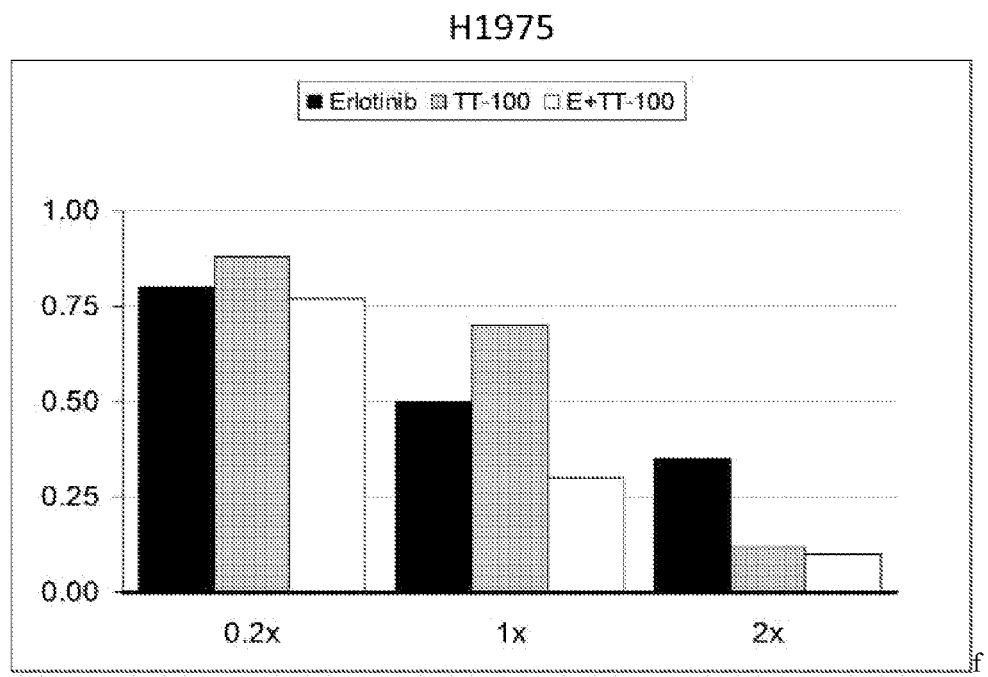

A combination of NDGA and Tarceva® (erlotinib) demonstrated synergy in a T790M cell line as illustrated in FIGS. 13A-B. FIG. 13B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

Figure 14:
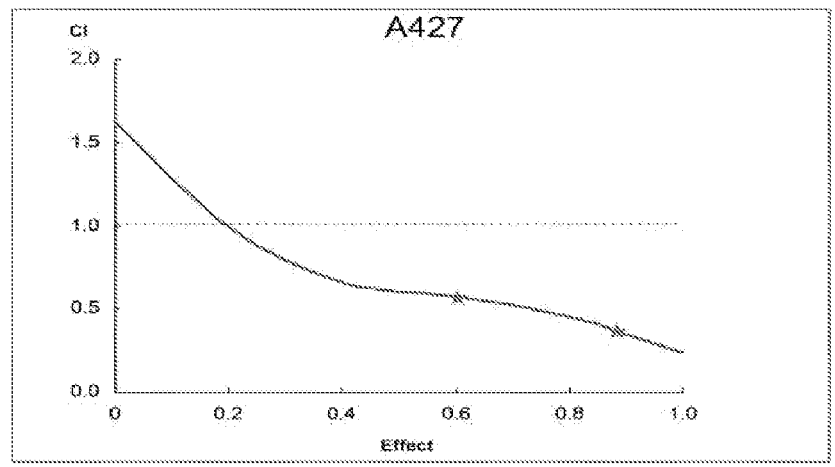
FIGS. 14A-B. CI (combination index) plots of NDGA (TT-100) in combination with erlotinib. The plots are used to quantitatively depict synergism (CI<1), additivity (CI=1), or antagonism (CI>1). The dotted line depicts the CI value of 1. The combination of NDGA and Tarceva® (erlotinib) also demonstrated synergy in a Kras mut cell line. These plots were generated from the data obtained from the combination dose effect curves using the Calcusyn software (FIG. 14A).
Figure 14:
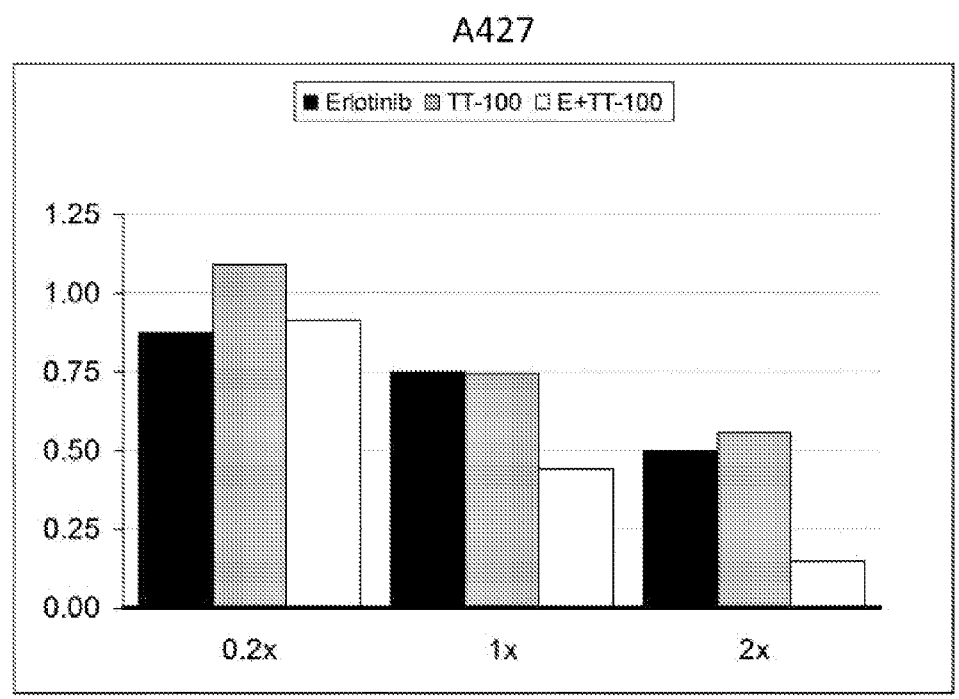

The combination of NDGA and Tarceva® (erlotinib) also demonstrated synergy in a Kras mut cell line as illustrated in FIGS. 14A-B. FIG. 14B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

Figure 15:
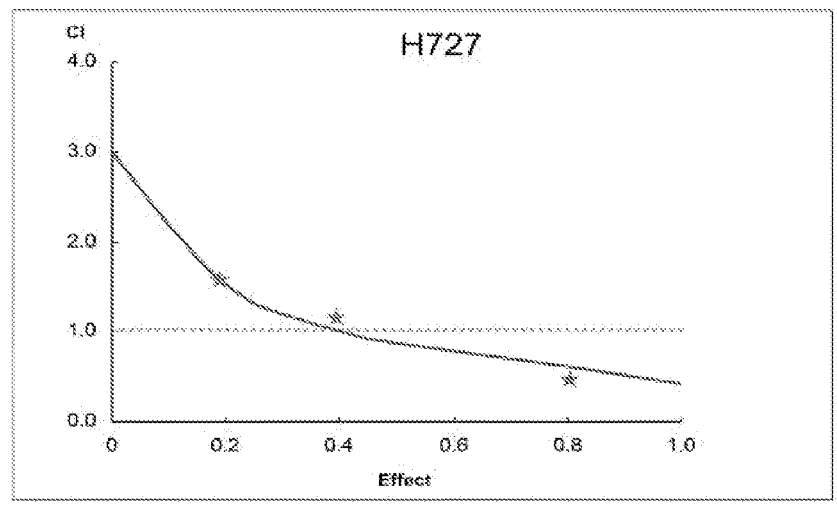
FIGS. 15A-B. CI (combination index) plots of NDGA (TT-100) in combination with erlotinib. The plots are used to quantitatively depict synergism (CI<1), additivity (CI=1), or antagonism (CI>1). The dotted line depicts the CI value of 1. The combination of NDGA and Tarceva® also demonstrated synergy in a second Kras mut cell line. These plots were generated from the data obtained from the combination dose effect curves using the Calcusyn software (FIG. 15A).
Figure 15:
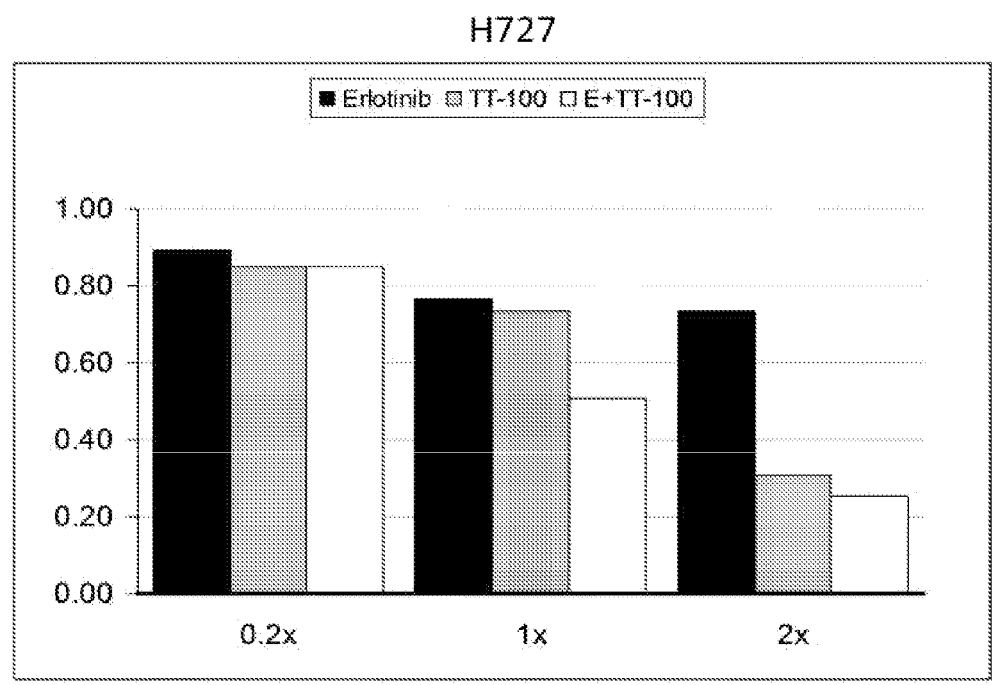

The combination of NDGA and Tarceva® also demonstrated synergy in a second Kras mut cell line as illustrated in FIG. 15. CI (combination index) plots of NDGA (TT-100) in combination with erlotinib in a H727 cell line. The plots are used to quantitatively depict synergism (CI<1), additivity (CI=1), or antagonism (CI>1). The dotted line depicts the CI value of 1. The combination of NDGA and Tarceva® also demonstrated synergy in a second Kras mut cell line. These plots were generated from the data obtained from the combination dose effect curves using the Calcusyn software (FIG. 15A). FIG. 15B shows drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM.

CI plots of NDGA (TT-100) in combination with erlotinib in lung BAC cell lines containing EGFR mutations were prepared. The plots are used to quantitatively depict synergism (CI<1), additivity (CI=1), or antagonism (CI>1). These plots were generated from the data obtained from the combination dose effect curves using the Calcusyn software. Drug interactions were tested using median-effect analysis on H1650 cells as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM. Non-additive or additive results were observed (data not shown).

CI (combination index) plots of NDGA (TT-100) in combination with erlotinib in lung BAC cell lines with Kras mutations were prepared. The plots are used to quantitatively depict synergism (CI<1), additivity (CI=1), or antagonism (CI>1). The dotted line depicts the CI value of 1. These plots were generated from the data obtained from the combination dose effect curves using the Calcusyn software. Drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM. Non-additive or additive results were observed (data not shown).

CI (combination index) plots of NDGA (TT-100) in combination with erlotinib in lung adenocarcinoma cell lines with EGFR mutations were prepared. The plots are used to quantitatively depict synergism (CI<1), additivity (CI=1), or antagonism (CI>1). The dotted line depicts the CI value of 1. These plots were generated from the data obtained from the combination dose effect curves using the Calcusyn software. Drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (erlotinib/TT100): 0.2×: 1.0 mM/3.0 mM; 1×: 5.0 mM/15.0 mM; and 2×: 10.0 mM/30.0 mM. Non-additive or additive results were observed (data not shown).

NDGA efficacy was shown in a range of xenografts of Table 3.

| Small Cell Lung (NCI-H209) | Breast (Her-2 over expressing) |
|---|---|
| Pancreatic (AsPC-1_ | Colon (LoVo) |
| Pancreatic (HPAC) | Cervical (C4-I) |
| Pancreatic (SW850) | Neuroblastoma |
| Breast (MDA-MB435) | NSCLC (NCI-H1264) |

Figure 16:
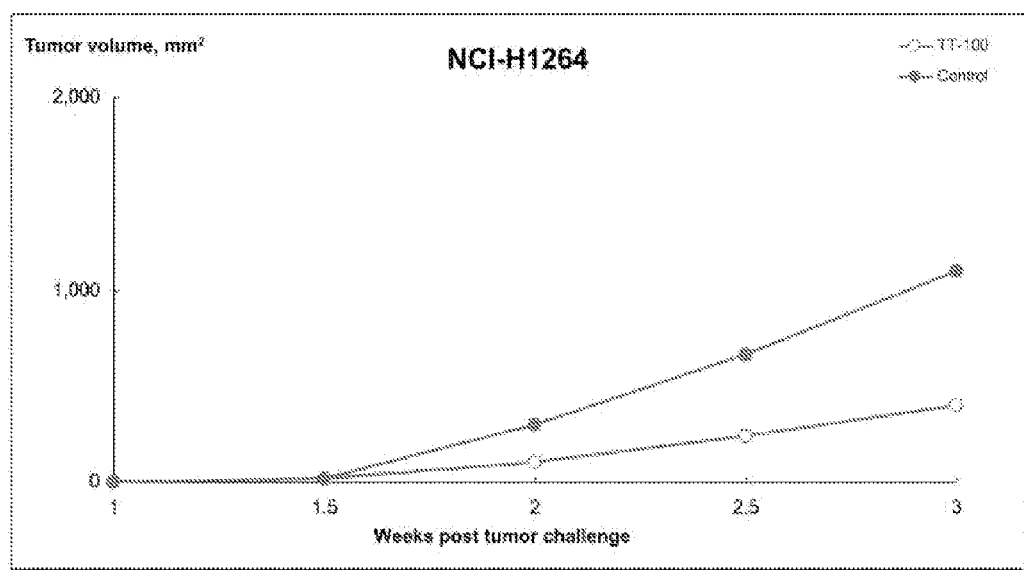
FIG. 16. NDGA (TT-100; open circules) was shown to inhibit tumor growth in a NSCLC xenograft 3 weeks post-tumor challenge compared to a control (closed circles). Tumor volume is shown (y axis) at 1, 2.5, 2, 2.5 and 3 weeks post tumor challenge (x axis).

NDGA (TT-100) was shown to inhibit tumor growth in a NSCLC xenograft 3 weeks post-tumor challenge compared to a control as illustrated in FIG. 16.

Figure 17:
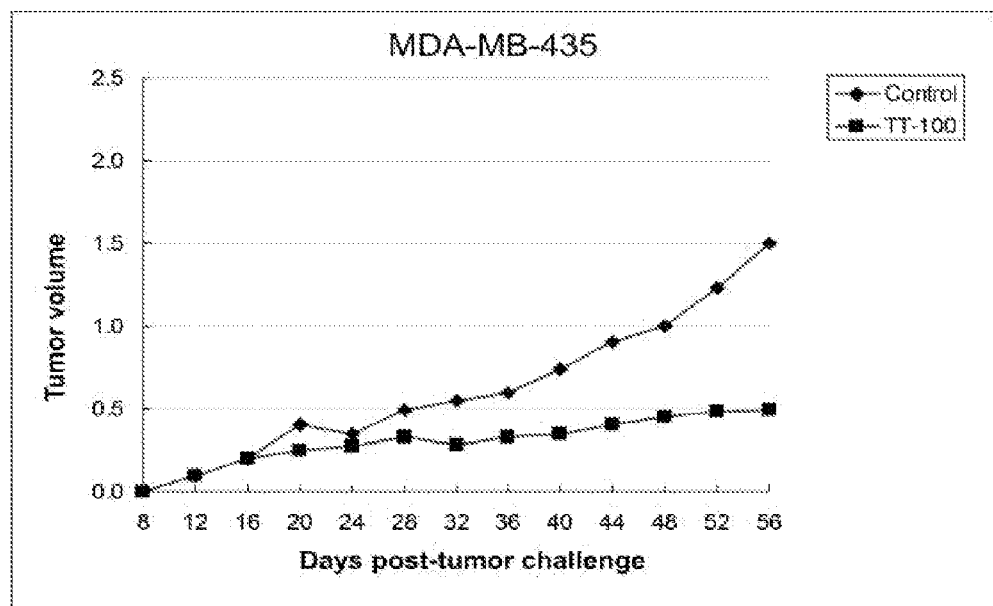
FIG. 17. NDGA (TT-100; squares) inhibited growth in a breast xenograft compared to a control (diamonds). Tumor volume is shown (y axis) at various time days post tumor challenge (x axis).

NDGA (TT-100) inhibited growth in a breast xenograft compared to a control as illustrated in FIG. 17.

Figure 18:
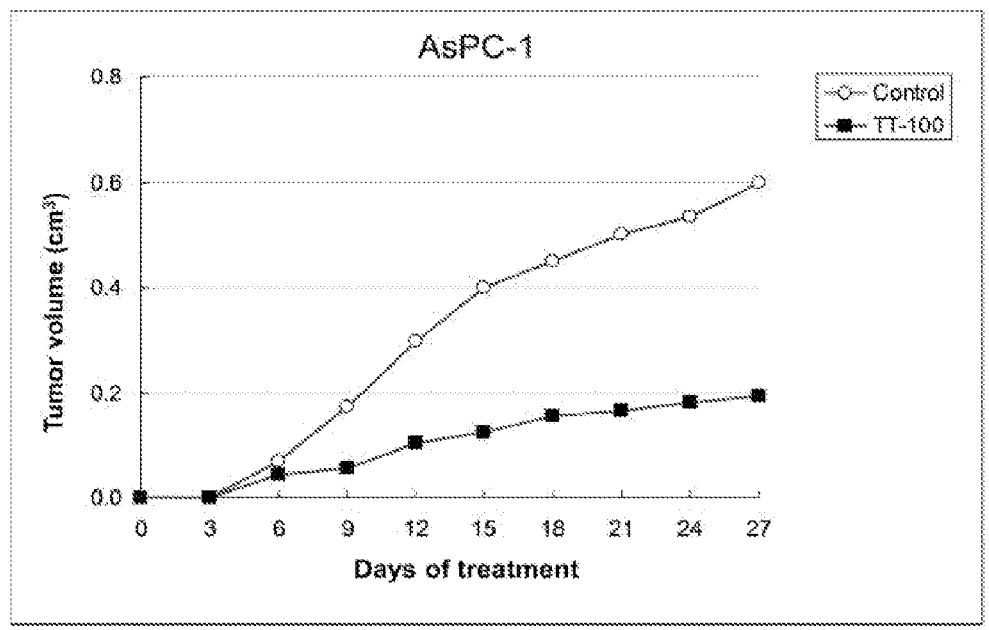
FIG. 18. NDGA (TT-100; closed squares) inhibited growth in a pancreatic xenograft compared to a control (open circles). Tumor volume is shown (y axis) at various time days post tumor challenge (x axis).

NDGA (TT-100) inhibited growth in a pancreatic xenograft compared to a control as illustrated in FIG. 18.

Figure 19:
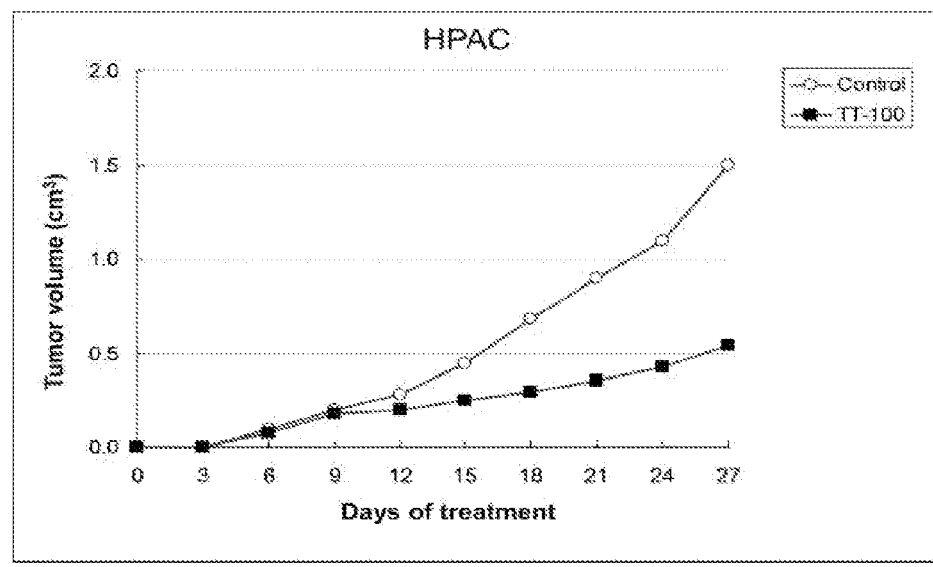
FIG. 19. NDGA (TT-100; closed squares) inhibited growth in a second pancreatic xenograft compared to a control (open circles). Tumor volume is shown (y axis) at various time days post tumor challenge (x axis).
Figure 20:
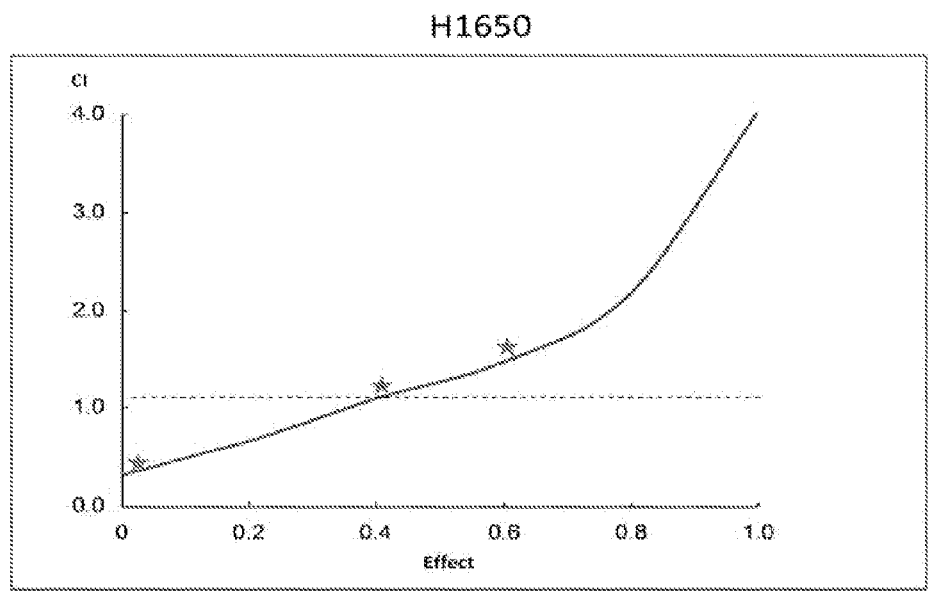
FIG. 20. CI (combination index) plots of NDGA (TT-100) in combination with erlotinib in lung BAC cell lines with EGFR mutations. The plots are used to quantitatively depict synergism (CI<1), additivity (CI=1), or antagonism (CI>1). The dotted line depicts the CI value of 1. The combination of NDGA and Tarceva® also demonstrated synergy in a H1650 cell line. These plots were generated from the data obtained from the combination dose effect curves using the Calcusyn software (FIG. 20A).
Figure 20:
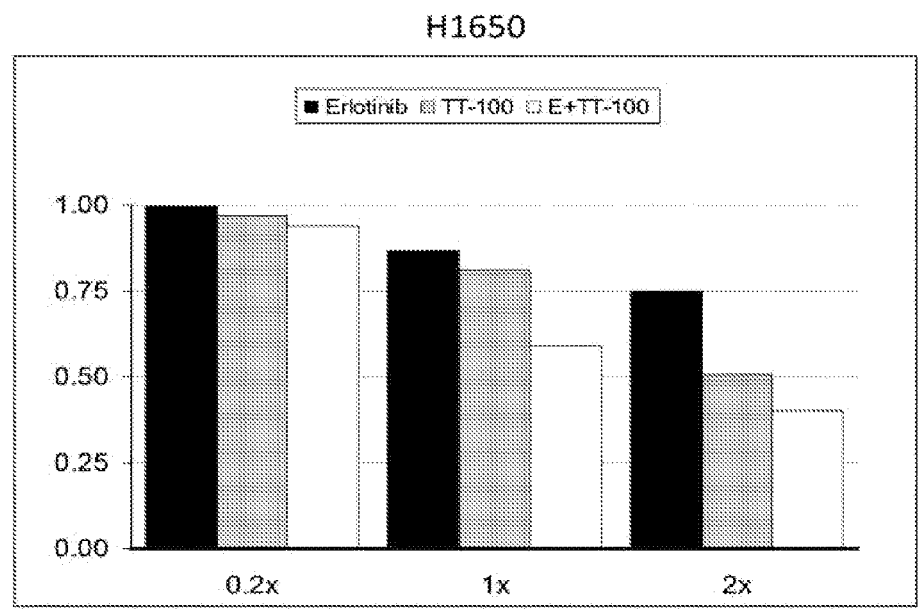
Figure 21:
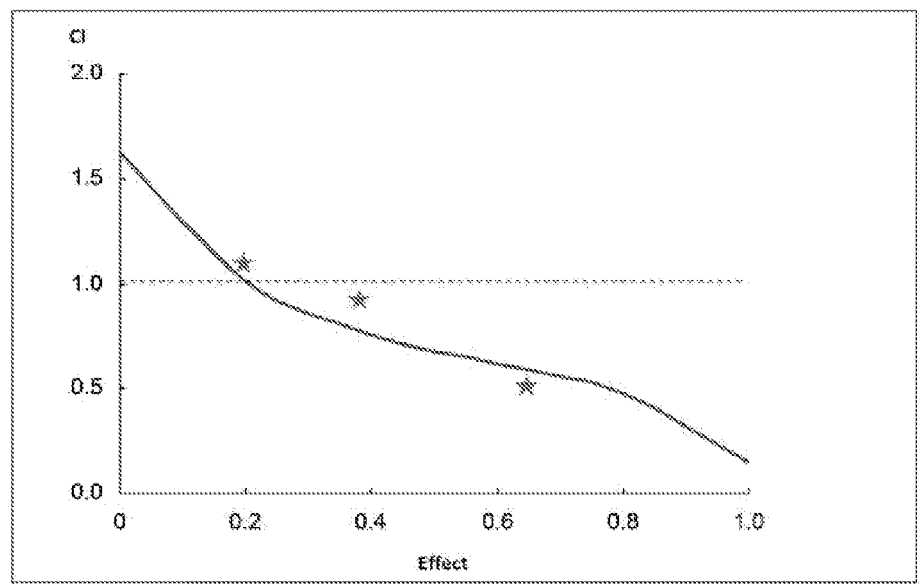
FIGS. 21A-B. CI (combination index) plots of NDGA (TT-100) in combination with erlotinib in lung carcinoma cell lines with Kras mutations. The plots are used to quantitatively depict synergism (CI<1), additivity (CI=1), or antagonism (CI>1). The dotted line depicts the CI value of 1. The combination of NDGA and Tarceva® also demonstrated synergy in a A549 cell line. These plots were generated from the data obtained from the combination dose effect curves using the Calcusyn software (FIG. 21A).
Figure 21:
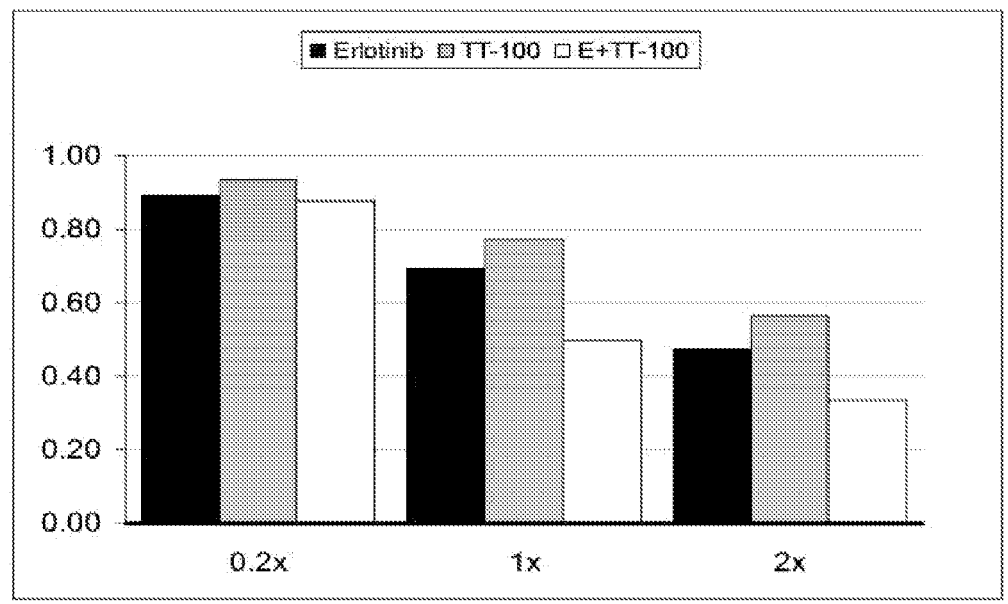
Figure 22:
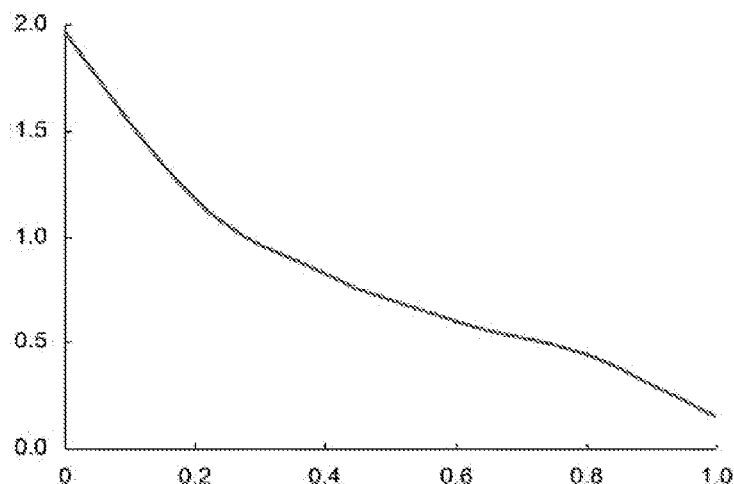
FIGS. 22A-B. CI (combination index) plots of NDGA (TT-100) in combination with erlotinib in lung carcinoma cell lines with Kras mutations. The plots are used to quantitatively depict synergism (CI<1), additivity (CI=1), or antagonism (CI>1). The dotted line depicts the CI value of 1. The combination of NDGA and Tarceva® also demonstrated synergy in a Calu-1 cell line. These plots were generated from the data obtained from the combination dose effect curves using the Calcusyn software (FIG. 22A).
Figure 22:
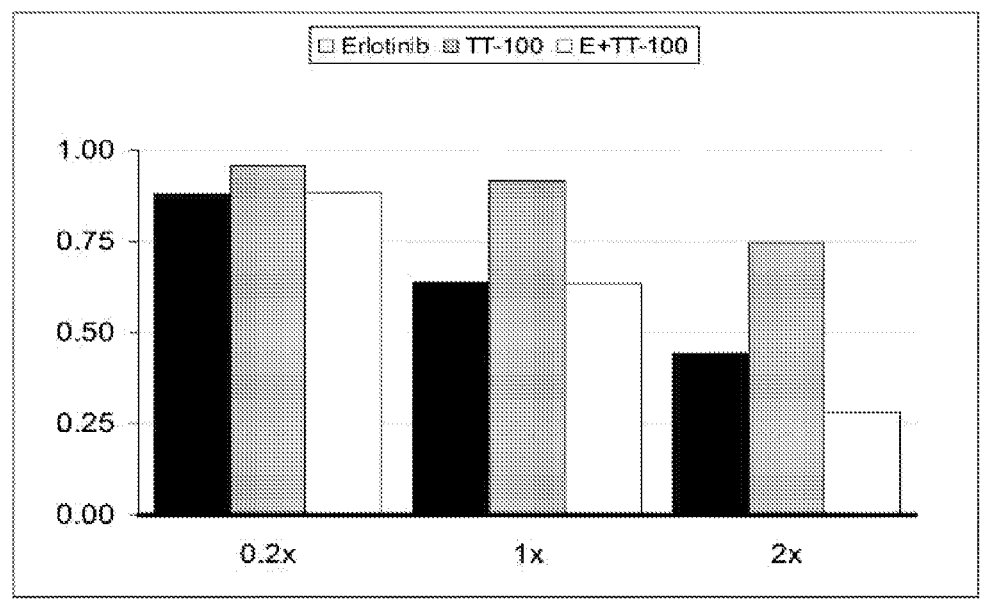
Figure 23:
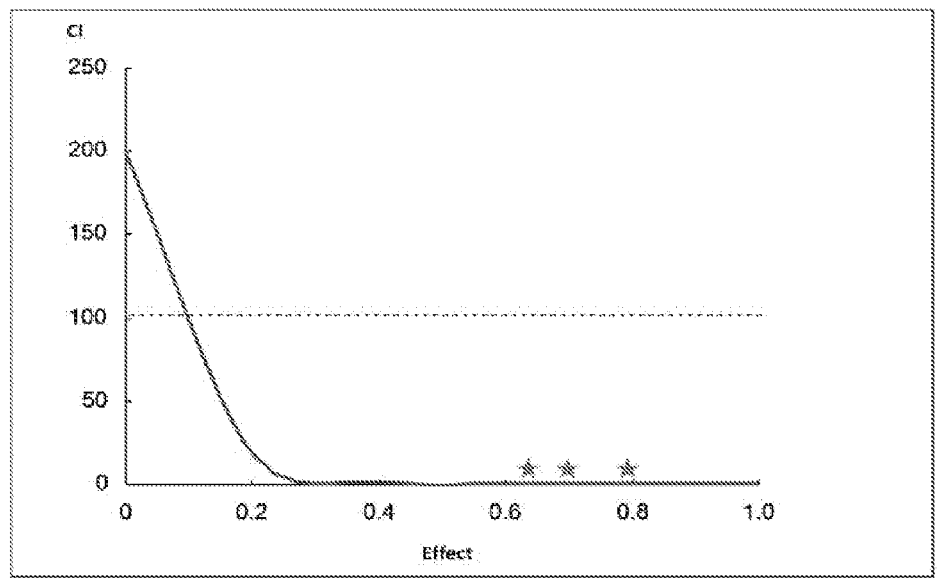
FIGS. 23A-B. CI (combination index) plots of NDGA (TT-100) in combination with erlotinib in lung BAC cell lines with EGFR/Kras mutations. The plots are used to quantitatively depict synergism (CI<1), additivity (CI=1), or antagonism (CI>1). The dotted line depicts the CI value of 1. The combination of NDGA and Tarceva® also demonstrated synergy in a H1666 cell line. These plots were generated from the data obtained from the combination dose effect curves using the Calcusyn software (FIG. 23A).
Figure 23:
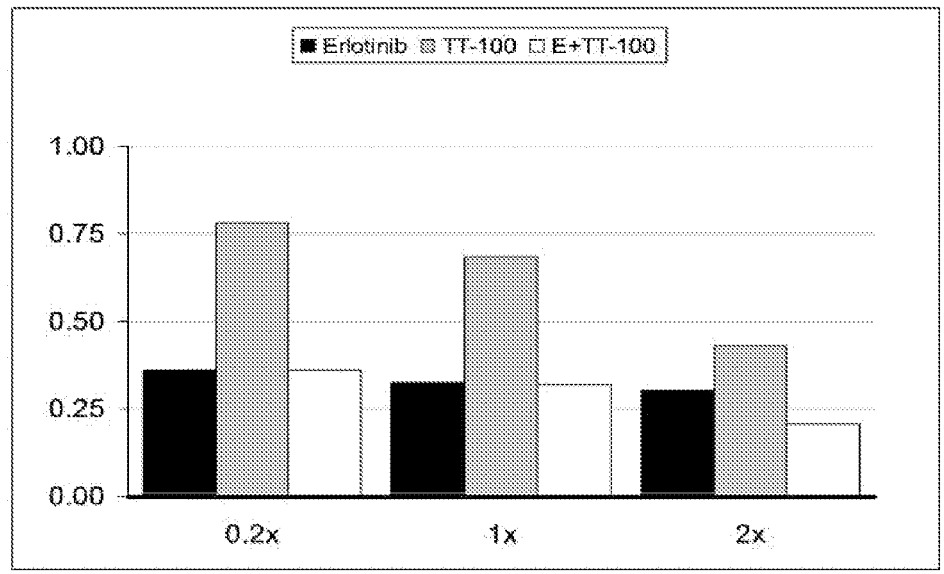
Figure 24:
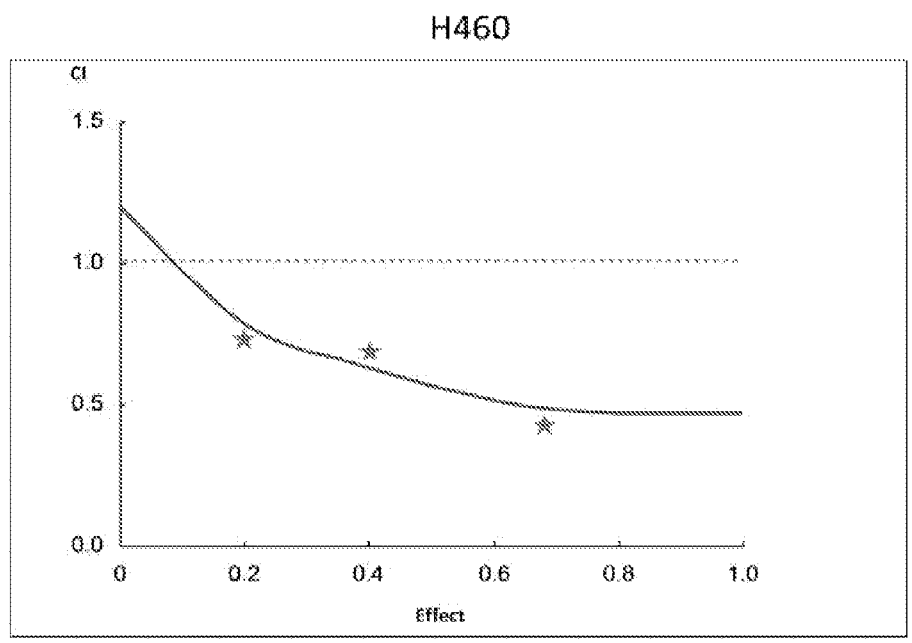
FIGS. 24A-B. CI (combination index) plots of NDGA (TT-100) in combination with erlotinib in large cell lines with Kras mutations. The plots are used to quantitatively depict synergism (CI<1), additivity (CI=1), or antagonism (CI>1). The dotted line depicts the CI value of 1. The combination of NDGA and Tarceva® also demonstrated synergy in a H460 cell line. These plots were generated from the data obtained from the combination dose effect curves using the Calcusyn software (FIG. 24A).
Figure 24:
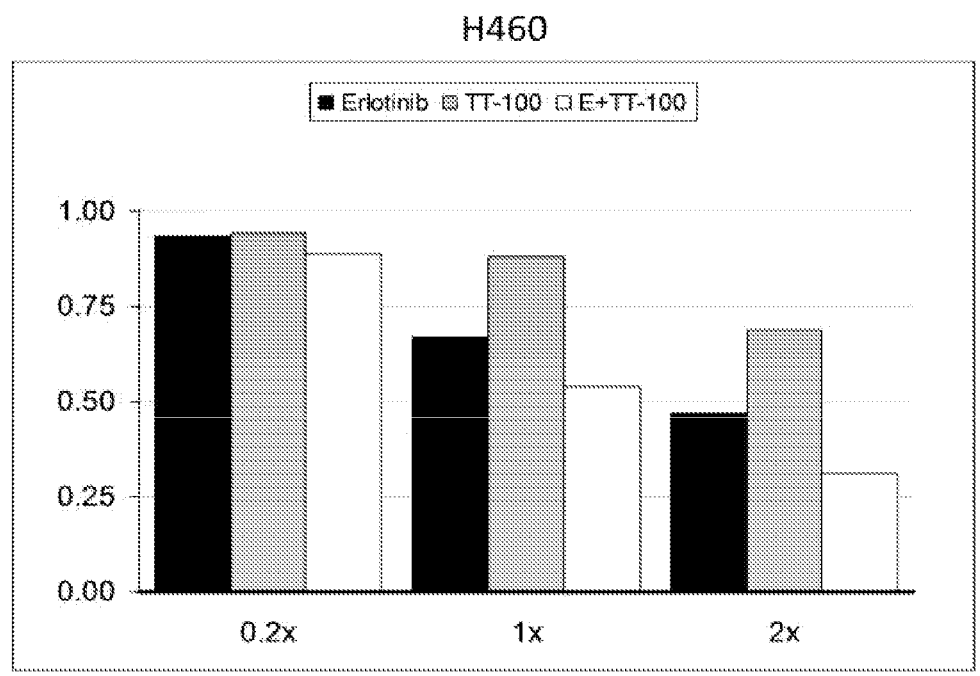
Figure 25:
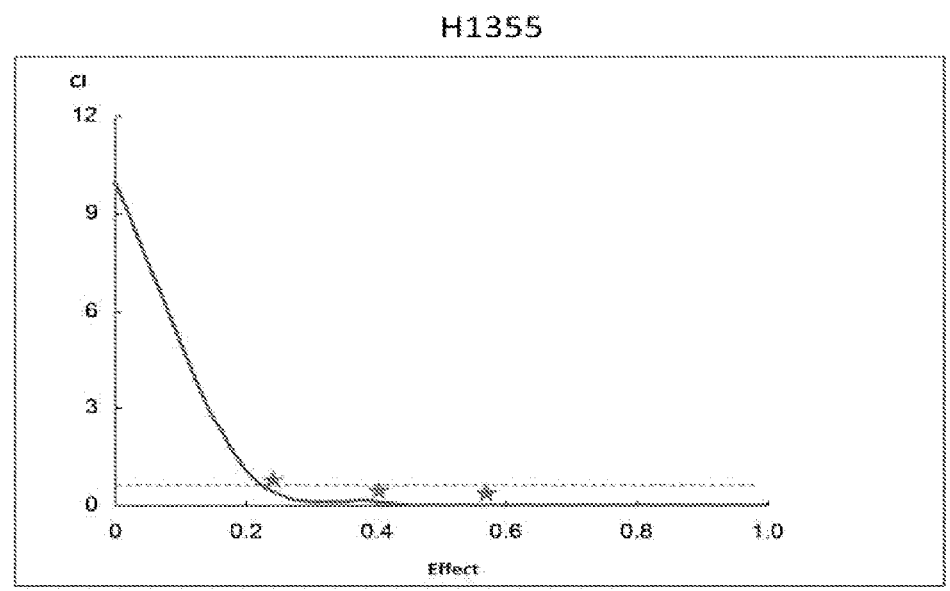
FIGS. 25A-B. CI (combination index) plots of NDGA (TT-100) in combination with erlotinib in lung carcinoma cell lines with Kras mutations. The plots are used to quantitatively depict synergism (CI<1), additivity (CI=1), or antagonism (CI>1). The dotted line depicts the CI value of 1. The combination of NDGA and Tarceva® also demonstrated synergy in a H1355 cell line. These plots were generated from the data obtained from the combination dose effect curves using the Calcusyn software (FIG. 25A).
Figure 25:
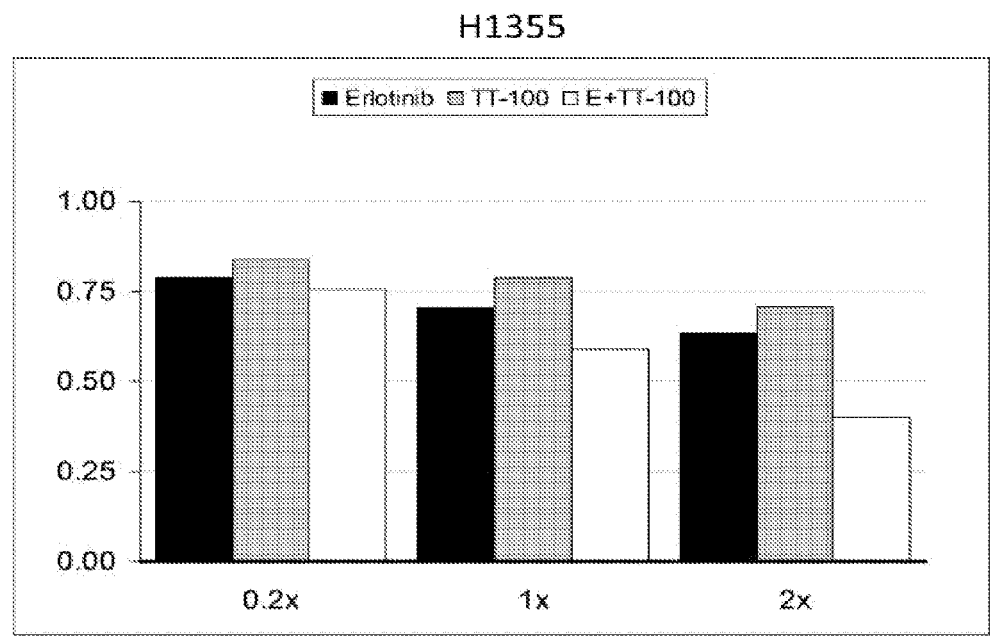
Figure 26:
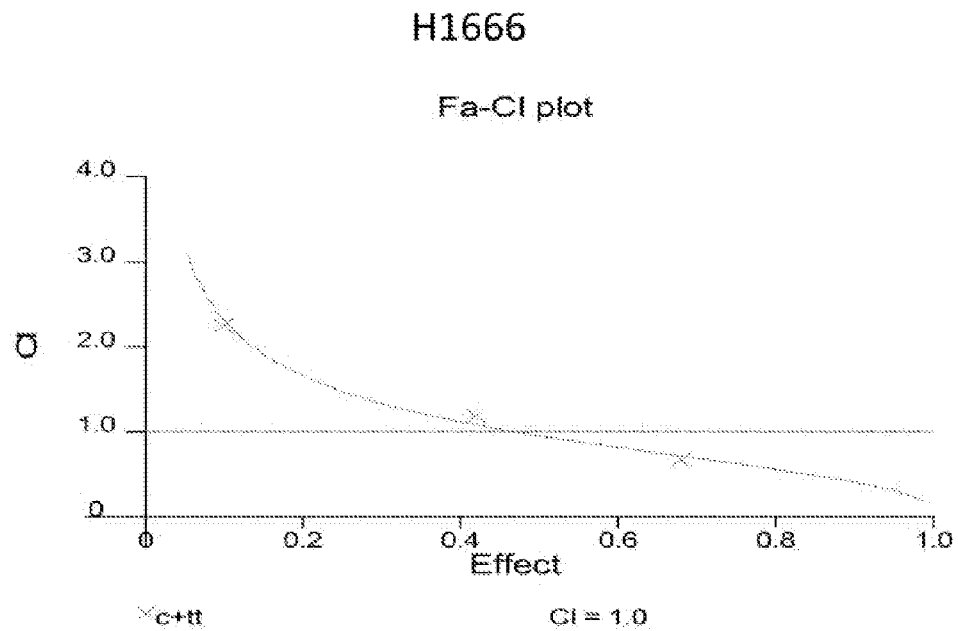
FIGS. 26A-B. CI (combination index) plots of NDGA (TT-100) in combination with cisplatin in a H1666 cell line. The combination of NDGA and cisplatin demonstrated synergy in a H1666 cell line. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software (FIG. 26A).
Figure 26:
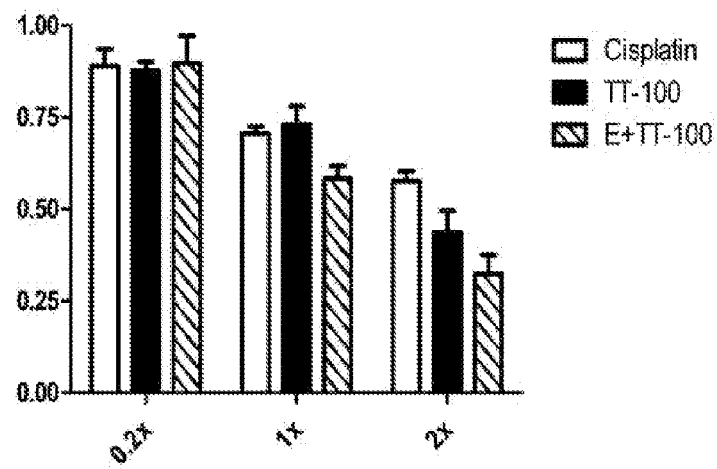
Figure 27:
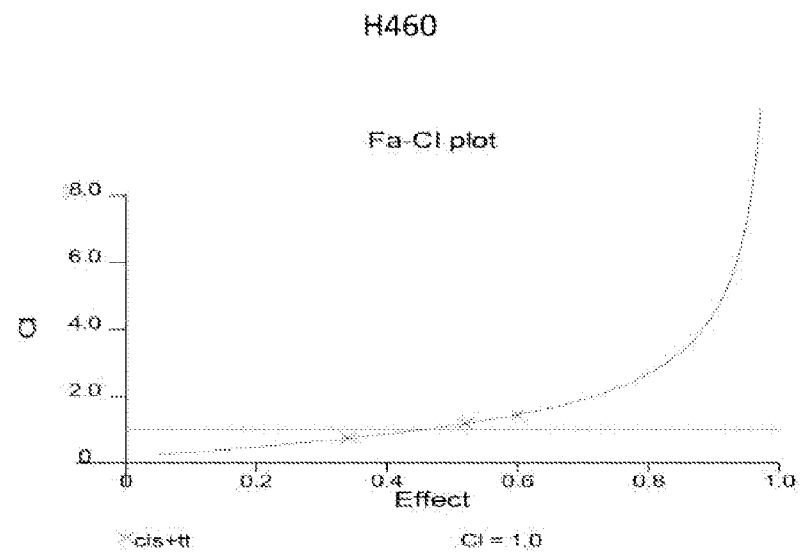
FIGS. 27A-B. CI (combination index) plots of NDGA (TT-100) in combination with cisplatin in a H460 cell line. The combination of NDGA and cisplatin demonstrated synergy in a H460 cell line. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software (FIG. 27A).
Figure 27:
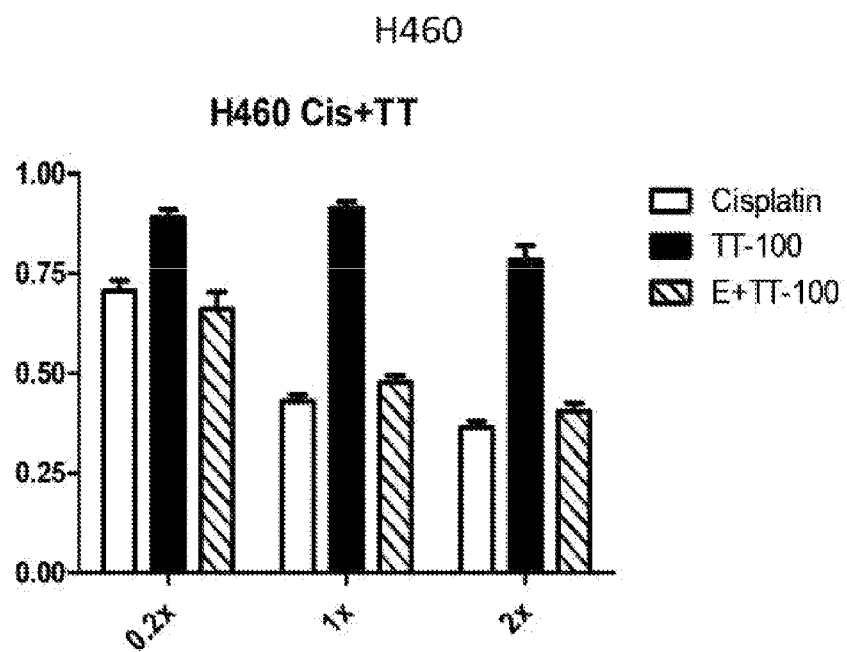
Figure 28:
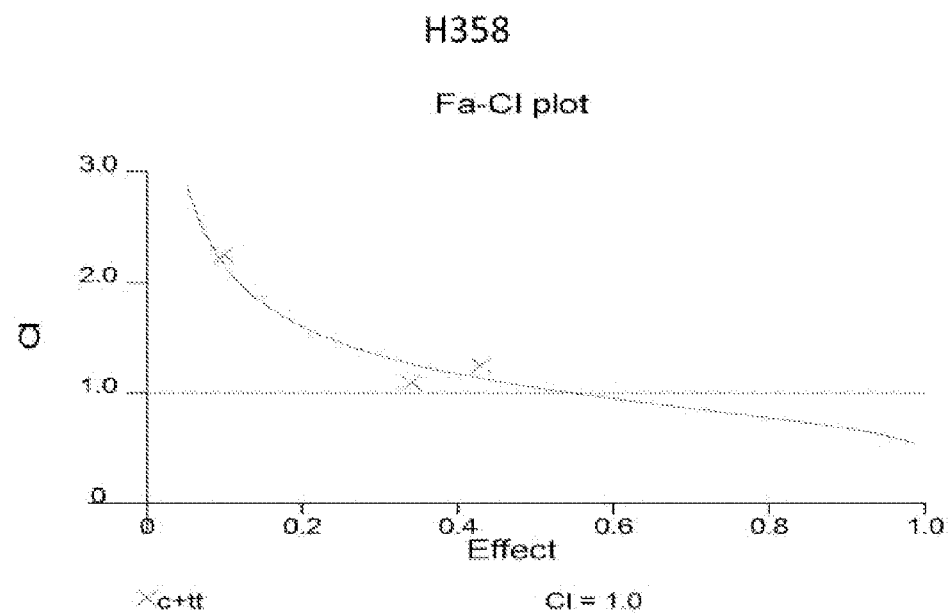
FIGS. 28A-B. CI (combination index) plots of NDGA (TT-100) in combination with cisplatin in a H358 cell line. The combination of NDGA and cisplatin demonstrated synergy in a H358 cell line. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software (FIG. 28A).
Figure 28:
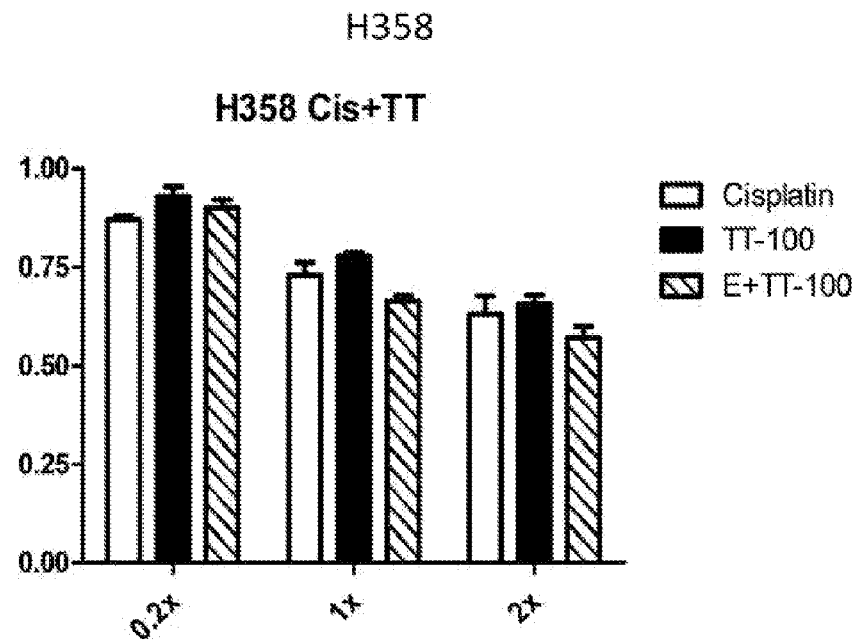
Figure 29:
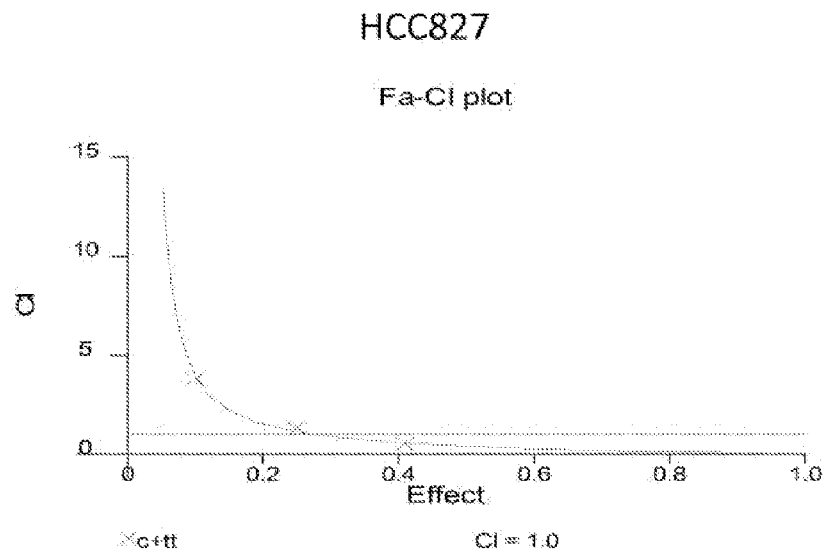
FIGS. 29A-B. CI (combination index) plots of NDGA (TT-100) in combination with cisplatin in a HCC827 cell line. The combination of NDGA and cisplatin demonstrated synergy in a HCC827 cell line. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software (FIG. 29A).
Figure 29:
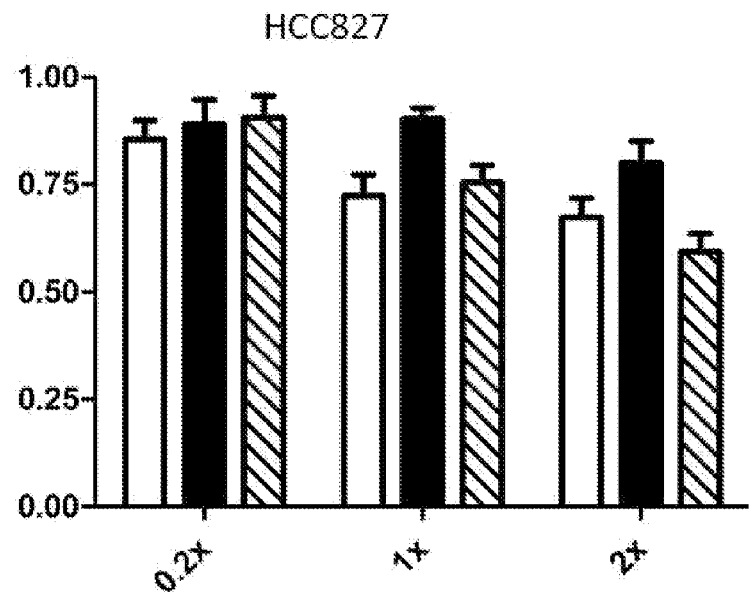

NDGA (TT-100) inhibited growth in a second pancreatic xenograft compared to a control as illustrated in FIG. 19.

Synergy of NDGA (>15 mM), with cisplatin was demonstrated in 4 of 11 NSCLC cell lines. Each cell line is listed at an effective dose of 25%, 50%, and 75%

TABLE 4

| Cell Line | ED25 | ED50 | ED75 |
|---|---|---|---|
| HCC827 | *1.136** | <u>0.401</u>+ | <u>0.146</u>+ |
| H1355 | *1.295** | *2.227** | *4.103** |
| H460 | <u>0.564</u>+ | *1.116** | *2.226** |
| H358 | *1.452 | 1.050** | <u>0.818</u>+ |
| H1666 | *1.480 | 0.958** | <u>0.628</u>+ |
| Calu-1 | *1.130** | *1.246** | *1.397** |
| A549 | *1.119** | *1.129** | *1.143** |
| H727 | ND | ND | ND |
| H1650 | 1.137* | *1.161** | *1.352** |
| A427 | 2.268* | *2.277** | *2.466** |
| H1975 | 1.723* | *1.474** | *1.315** |

Non-additive effects are shown in italics with an asterisk. Additive effects are shown in bold text. Synergistic effects are shown in underlined text with a "+" symbol. ND = not determined.

The effects of combination treatment with NDGA (TT-100) and cisplatin are illustrated in the Figures. Synergistic effects were observed in cell lines HCC827 (lung adenocarcinoma cell line with EGFR mutations), H460 (large cell with KRAS mutations), H358 (lung BAC with Kras mutations) and H1666 (lung BAC with EGFR and Kras wt).

The data obtained from these experiments led the present inventors to believe consider that NDGA (TT-100) is synergistic with Tarceva/Iressa, first, because of its non ATP binding characteristics that allow the combination to simultaneously target the mutated EGFR at both the ATP binding site where Tarceva binds and at the substrate binding sight where TT-100 binds. This gives the combination two chances to inhibit EGF signaling. Secondly, the data also indicates that NDGA (TT-100) inhibits other kinase pathways central to a tumor cell's ability to develop resistance to Tarceva/Iressa. Consequently, synergy can be created by inhibiting one of those pathways (IGF-1R and/or c-Met) in addition to the EGFR inhibition from Tarceva/Iressa.

CI (combination index) plots of NDGA (TT-100) in combination with cisplatin in a H1975 cell line. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software. Drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM. Non-additive or additive results were observed (data not shown).

CI (combination index) plots of NDGA (TT-100) in combination with cisplatin in an A427 cell line were prepared. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software. Drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM. Non-additive or additive results were observed (data not shown).

CI (combination index) plots of NDGA (TT-100) in combination with cisplatin in an A549 cell line were prepared. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software. Drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM. Non-additive or additive results were observed (data not shown).

CI (combination index) plots of NDGA (TT-100) in combination with cisplatin in a Calu-1 cell line were prepared. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software. Drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM. Non-additive or additive results were observed (data not shown).

CI (combination index) plots of NDGA (TT-100) in combination with cisplatin in a H1355 cell line. The plots are used to quantitatively depict synergism (CI<1), additivity (CI=1), or antagonism (CI<1). The dotted line depicts the CI value of 1. These plots were generated from the data obtained from the combination dose effect curves using the Calcusyn software. Drug interactions were tested using median-effect analysis as described by Chou and Talalay. A fixed ratio for each drug was used as a single-agent or in combination for three doses. Based on this data a combination index (CI) was generated using Calcusyn to quantitatively determine the interaction between the drugs. Dose (cisplatin/TT100): 0.2×: 1.0 mM/3.0 mM; 1×: 5.0 mM/15.0 mM; and 2×: 10.0 mM/30.0 mM. Non-additive or additive results were observed (data not shown).

EXAMPLES

The application may be better understood by reference to the following non-limiting examples, which are provided as exemplary embodiments of the application. The following examples are presented in order to more fully illustrate embodiments and should in no way be construed, however, as limiting the broad scope of the application. While certain embodiments of the present application have been shown and described herein, it will be obvious that such embodiments are provided by way of example only. Numerous variations, changes, and substitutions may occur to those skilled in the art; it should be understood that various alternatives to the embodiments described herein may be employed in practicing the methods described herein.

Example 1

Modeling NDGA Interaction With the IGF-1R Substrate Binding Site

It was hypothesized that NDGA might act as a substrate competitive inhibitor of the IGF-1R, a new mechanism among the myriad ATP analogs being developed as RTK inhibiting agents. To test this hypothesis, the inhibition of IGF-1R tyrosine kinase activity (i.e., phosphorylation) in the presence and absence of 20 µg/ml NDGA was assessed at varying concentrations of artificial substrate (poly 4:1 Glu:Tyr). The ability of NDGA to inhibit phosphorylation of a peptide substrate by purified IGF-1R kinase domain across a range of substrate concentrations was determined. A Lineweaver-Burke analysis was used to calculate Km and Vmax for this reaction (FIG. 1).

As depicted in FIG. 1, NDGA reduced the affinity of the PGT substrate for the IGF-1R protein, without affecting the maximal reaction velocity (at maximal amounts of PGT. These results are consistent with a substrate competition mechanism of action, where NDGA competes with PGT to the substrate binding site on the IGF-1R. At lower amounts of substrate, NDGA can successfully compete off the PGT to reduce substrate phosphorylation activity. At a theoretical infinite amount of PGT substrate (1/[PGT]=0) NDGA cannot compete and the reaction occurs at its maximal rate. With non-competitive inhibition, an inhibitory effect of NDGA would still be observed at maximal amounts of PGT substrate. These data are suggestive of substrate competition by NDGA on the kinase domain of the IGF-1R.

Example 2

Effect of NDGA on the Ability of the IGF-1R to Phosphorylate Exogenous Substrates The effects of NDGA on the ability of the IGF-1R to phosphorylate exogenous substrates were determined by an in vitro tyrosine kinase assay. Soluble IGF-1R, partially purified from CHO-IGFR cells were incubated with 10 nM IGF-1 in Kinase Buffer (50 mM, pH 7.4, 150 mM NaCl, 0.1% Triton X-100, 0.1% gelatin, 5 mM $MnCl_2$, 8 mM $MgCl_2$, and 1 mM PMSF) for 1 hr at room temperature (RT). Next, NDGA or vehicle was added to a final reaction concentration of 20 µg/ml. Labeled $^{32}$P-ATP (20 µM) was added in the presence of varying concentrations of the tyrosine kinase substrate poly Glu4:Tyr1 (PGT) (0.005 to 4 mg/ml). The reaction was stopped after 30 min at 22° C. by blotting 40 µl of the reaction mixture onto Whatman 3 MM papers. Filter papers were air dried and then subjected to the following washing protocol in 10% TCA with 10 mM $Na_4P_2O_7$: 15 min at 4° C., 15 min at 20° C., 5 min boiling, 5 min boiling, followed by a short rinse with acetone. The filter papers were then allowed to air dry completely. $^{32}$P incorporation into the substrate was determined by liquid scintillation counting.

Next, competition with ATP was determined directly by employing an assay previously validated to quantify the Km for small molecule kinase inhibitors compete for ATP binding to various kinases (Goldstein et al. 2008). NDGA did not interfere with binding of a labeled ATP analog to recombinant IGF-1R at concentrations shown to inhibit IGF-1R kinase activity, or any concentration of NDGA up to 100 µM (FIG. 2).

Example 3

Computer Modeling

Figure 3:
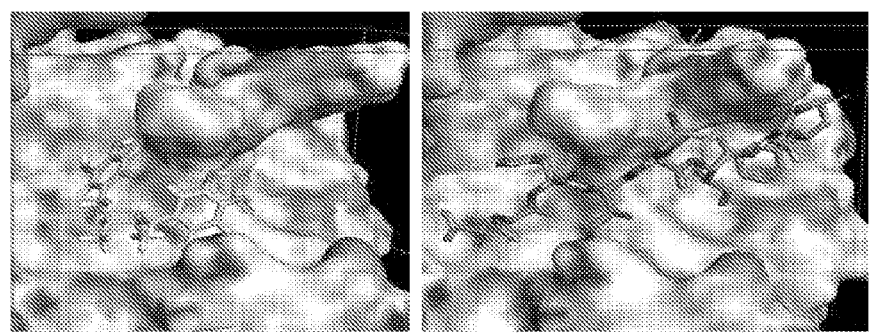
FIG. 3. Results of computational modeling of the IGF-1R kinase domain. An active-site box for the docking simulation was defined around the peptide substrate (A) as positioned in the co-crystallized structure. (B) Computational docking of NDGA into the substrate-binding site of IGF-1R. Docking was performed with the FRED2 suite of programs (OpenEye) utilizing an X-ray crystal structure of the kinase domain (PDB=1K3A) and a library of NDGA conformations produced by OMEGA (OpenEye). Visualization was performed with PYMOL (DeLano Scientific).

Computer modeling was used to determine the ability of NDGA to fit into the substrate binding site on the receptor beta subunit, which could explain the inhibition of autophosphorylation observed in the purified kinase domain peptides. Employing data on the crystal structure of the kinase domain (56) and the Amber8 program, the fit of NDGA was modeled into the substrate binding site of the kinase domain (FIG. 3). Although NDGA largely employed contact points distinct from a synthetic substrate, the compound displayed a strong fit within the binding site. Additionally, although the orientation did not support the model of Blum et al., the data suggest that the catechols of NDGA act as tyrosine mimics. The present inventors theorize that NDGA acts as a substrate competitive inhibitor.

Example 4

Toxicology Studies

A rat 28-day multi-dose toxicology assessment was conducted at 15, 150, or 500 mg/kg/day. No effect was observed at 15 mg/kg/day. Stomach and duodenal hypertrophy/alterations were observed at 150 and 500 mg/kg.

A dog 28-day multi-dose toxicology assessment was also conducted. No observable effect level (NOEL) was observed at 60 mg/kg/day. Necropsy findings limited to intestinal mucosal reddening.

The table below provides a summary of Acute IND enabling Toxicology Studies.

| Study Type | Species/ Strain | Number/ Sex/ Group | Dose/ Interval/ Duration | Route of Administration | Systematic Exposure | Results |
|---|---|---|---|---|---|---|
| Acute Toxicity | CR: 1CD BR rats | 5 males and 5 females | Single doses of 100, 300, 1000, 3000 or 5000 mg/kg | Oral (gavage) | Rats received single doses of TT-100 and were observed for 14 days | The acute oral $LD_{50}$ of TT-100 was greater than 5000 mg/kg. The 100 mg/kg dose was considered to be the no-effect level, due to the lack of clinical signs and gross lesions seen |
| Acute Toxicity | New Zealand white rabbits | 5 males and 5 females | Single doses of 100, 300, 1000, 3000 or 5000 mg/kg | Oral (gavage) | Rabbits received single doses of TT-100 and were observed for 14 days | Acute oral $LD_{50}$ values were 2500 and 1650 mg/kg for male and female rabbits, respectively. A dose of 1000 mg/kg was identified as the no-effect level |

A summary of chronic IND enabling toxicology studies are identified in the following table:

| Study Type | Species/ Strain | Number/ Sex/ Group | Dose/ Interval/ Duration | Route of Administration | Systematic Exposure | Results |
|---|---|---|---|---|---|---|
| Multi-dose Toxicity | Beagle dogs | 4 males and 4 females | 0, 60, 200 or 600 mg/kg for 30 days | Oral (capsule) | Dogs received 0, 60, 200 or 600 mg/kg/day for 30 days. On Days 0 and 29, blood was collected at various post-dosing intervals | 2 females that received the 600 mg dose experienced deterioration and significant loss of body weight and were sacrificed prior to study completion. At this dose, several clinical signs and symptoms, hematological and clinical changes were seen. Gross pathological evaluation of the 2 females terminated prior to study completion showed reddened mucosa in the stomach and intestinal tract. Absolute/relative organ weight changes were seen at the 600 mg dose All of the other doses appeared to be well-tolerated in this study |
| Multi-dose Toxicity | Sprague Dawley rats | 10 males and 10 females | Doses of 0, 15, 150 and 500 mg/kg, once daily for 28 days | Oral (gavage) | Rats received daily doses of TT-100 for 28 days | The stomach and duodenum appeared to be the primary target organs of toxicity, with adverse events occurring at 150 and 500 mg/kg/ day. The no-effect dose level was identified as 15 mg/kg/day |
| Multi-dose Toxicity (Dose Escalation) | Beagle dogs | 2 males and 2 females | Escalation Phase: 100, 300, 600 and 1200 mg/kg Repeated Dose Phase: 300 mg/kg/day for 6 days | Oral (capsule) | Dogs received single doses, beginning at 100 mg/kg and continuing to 300, 600 and 1200 mg/kg to identify the maximum repeatable dose. In the repeated dose phase, 300 mg/kg was administered for 6 days | Significant emesis, diarrhea and darkened stools were observed at doses of 600 and 1200 mg/kg. During the repeated dose part of the study, the 300 mg/kg dose was fairly well tolerated, with limited emesis and diarrhea |

Example 5

Clinical Trials

Phase 1B Tarceva Failure NSCLC Study Design:

Second line therapy for EGFR mutated patients who develop resistance to Tarceva/Iressa. Biopsy upon relapse to determine T790M status and genetic profile Two arm multi-dose, dose escalating design: TT-100 N=15/arm (30 total).

Arm 1 (T790M positive biopsy, after developing resistance).

Arm 2 (T790M negative biopsy, after developing resistance).

Primary and secondary end points may be assessed:

Primary: MTD and PK/PD (Affect on biological markers/target kinase).

Secondary: ORR/CBR.

Phase 2 POC Tarceva® Failure NSCLC Study Design:

Second line therapy for EGFR mutated patients who develop resistance to Tarceva®

Randomized open label design: Standard of care±TT-100 N=60/arm (120 total)

End points: Primary: Progression Free Survival. Secondary: ORR/CBR and Overall Survival.

Phase 2 Trials may be used to assess Tarceva® failure in the treatment of metastatic NSCLC (N~120).

Phase 3 Trials may be used to assess Tarceva® failure in the treatment of metastatic NSCLC (N~500) or locally advanced NSCLC.

Additional EGF, cMet, IGF driven tumors may be analyzed for sensitivy to treatment with a method described herein: Pancreatic, Colorectal, Glioma, Breast and Esophageal.

The methods described herein may be used to treat lung cancer (e.g., NSCLC) in patients who relapse after treatment with Tarceva® or Iressa®.

TT-100 provides a superior safety profile and represents the only inhibitor of all 3 key signaling pathways. Additionally, TT-100 is the first inhibitor shown to completely circumvent the T790M mutation.

Administration of TT-100 inhibits tumor growth via inhibition of EGFR and IGF1R. Administration of TT-100 inhibits angiogenesis via inhibition of c-met and VEGFR2. Administration of TT-100 inhibits metastasis via inhibition of c-met and IGF1R.

Example 6

Clinical Trials With Refractory Patients

Primary objectives of the study are to determine the maximum tolerated dose of NDGA (TT-100) plus erlotinib (erlotinib hydrochloride) in patients with non-small cell lung cancer (NSCLC) that are refractory to erlotinib.

Secondary objectives are to describe the toxicity profile of NDGA (TT-100) plus erlotinib, to determine the preliminary efficacy of NDGA (TT-100) plus erlotinib, and to characterize the pharmacokinetic behavior of the combination.

This is a dose-escalation study. Patients receive NDGA (TT-100) orally (PO) twice daily (BID) and erlotinib hydrochloride PO once daily (QD) on days 1-28. Courses repeat every 28 days in the absence of disease progression or unacceptable toxicity.

After completion of study treatment, patients are followed up for 30 days.

Interventions
  Drug: NDGA (TT-100) given PO
  Drug: erlotinib hydrochloride given PO
Arms, Groups and Cohorts
  Experimental: Treatment (NDGA (TT-100), erlotinib). Patients receive NDGA (TT-100) PO BID and erlotinib hydrochloride PO QD on days 1-28. Courses repeat every 28 days in the absence of disease progression or unacceptable toxicity.
Clinical Trial Outcome Measures
  Primary Measures
    Maximum tolerated dose (MTD) of NDGA (TT-100) and erlotinib, determined according to incidence of dose-limiting toxicity (DLT) graded using the National Cancer Institute (NCI) Common Terminology Criteria for Adverse Events (CTCAE) V4; time frame: Up to 28 days after a full course of therapy.
  Secondary Measures
    Toxicities as measured by NCI CTCAE V4 time frame: Up to 30 days
    Overall response rate among patients with measurable disease, measured by RECIST 1.1, Time Frame: Up to 30 days.
    Disease control rate, measured by RECIST 1.1, time frame: Up to 30 days
    Progression-free survival time frame: duration of time from start of treatment to time of progression or death, assessed up to 30 days.
    Overall survival time frame: duration of time from the start of treatment to death from any cause, assessed up to 30 days.
    Concentrations of NDGA (TT-100) in plasma, measured by liquid chromatography-tandem mass spectrometry (LC-MS/MS) assay; Time Frame: Days 15-16 of course 1, days 1 and 15 of course 2, and day 1 of courses 3-4.
Participating in the Clinical Trial
  Inclusion Criteria
    Patients must provide written informed consent prior to any screening procedures, willing and able to comply with scheduled visits, treatment plan and laboratory tests.
    Patient is able to swallow and retain oral medication.
    Histologically or cytologically documented diagnosis of NSCLC.
    Tumor tissue for correlative studies is mandatory.
    Previously received treatment with a single-agent erlotinib.
    Systemic progression of disease (Response Evaluation Criteria in Solid Tumors [RECIST] or World Health Organization [WHO]) while on continuous treatment with cisplatin, gefitinib or erlotinib.
    Patients must have measurable disease; disease in previously irradiated sites is considered measurable if there is clear disease progression following radiation therapy.
    Failed 1-2 prior chemotherapies for advanced disease; prior erlotinib is allowed in the dose finding phase and expansion cohort A.
    Patients must be willing to be off therapy for a minimum of two weeks (In expansion cohort A patients on erlotinib do not have to discontinue treatment).
    Eastern Cooperative Oncology Group (ECOG) performance status 0-2.
    Life expectancy greater than 3 months.
    Hemoglobin>9 g/dL (International System [SI] units: 90 g/L) without transfusion support or growth factors within 10 days of starting INC280.
    Platelet count>=75×10^9/L.
    Absolute neutrophil count (ANC)>=1.2×10^9/L without growth factor support.
    Total bilirubin=<2× upper limit of normal (ULN).

Aspartate aminotransferase (AST)/serum glutamic oxaloacetic transaminase (SGOT) and/or alanine aminotransferase (ALT)/serum glutamate pyruvate transaminase (SGPT)=<2.5× upper limit of normal (ULN).

Serum creatinine=<2×ULN.

Serum amylase=<ULN.

Serum lipase=<ULN.

Fasting serum triglyceride level=<500 mg/dL.

Exclusion Criteria

Patients who have had major surgery within 4 weeks of initiation of study medication, excluding the placement of vascular access.

Patients with concurrent uncontrolled medical conditions that may interfere with their participation in the study or potentially affect the interpretation of the study data.

Unstable angina pectoris, symptomatic congestive heart failure, myocardial infarction=<6 months prior to first study treatment, serious uncontrolled cardiac arrhythmia.

Severely impaired lung function.

Active (acute or chronic) or uncontrolled infection.

Nonmalignant medical illnesses that are uncontrolled or whose control may be jeopardized by the treatment with the study therapy.

Liver disease (i.e. cirrhosis, chronic active hepatitis, chronic persistent hepatitis).

Symptomatic central nervous system (CNS) metastases that are neurologically unstable or requiring increasing doses of steroids to control CNS disease.

Patients with controlled CNS metastases are allowed; radiotherapy or surgery for CNS metastases must have been completed>2 weeks prior to study entry; patients must be neurologically stable, having no new neurologic deficits on clinical examination, and no new findings on CNS imaging; steroid use for management of CNS metastases must be at a stable dose for two weeks preceding study entry.

Receiving drugs known to be strong inducers of cytochrome P450 3A4 (CYP3A4) or inhibiting drugs known to interact with erlotinib including, but not limited to: enzyme-inducing anticonvulsants, rifampicin, rifabutin, St John wort and ketoconazole.

Treatment with proton pump inhibitors within 3 days prior to study entry.

Currently receiving any prohibited medications including vitamins and herbal supplements.

Any other condition that would, in the investigator's judgment, contraindicate participation in the clinical study due to safety concerns or compliance with clinical study procedures, e.g., infection/inflammation, intestinal obstruction, unable to swallow medication, social/psychological issues, etc.

Pregnant or nursing (lactating) women, where pregnancy is defined as the state of a female after conception and until the termination of gestation, confirmed by a positive human chorionic gonadotropin (hCG) laboratory test (>5 mIU/mL).

Women of child-bearing potential, defined as all women physiologically capable of becoming pregnant, unless they are using highly effective methods of contraception during dosing and for 3 months after stopping study drug; highly effective contraception methods include: total abstinence, male or female sterilization or a combination of any two of the following (a+b or a+c or b+c): (a) Use of oral, injected or implanted hormonal methods of contraception; (b) Placement of an intrauterine device (IUD) or intrauterine system (IUS); (c) Barrier methods of contraception: condom or occlusive cap (diaphragm or cervical/vault caps) with spermicidal foam/gel/film/cream/vaginal suppository.

Women are considered post-menopausal and not of child bearing potential if they have had 12 months of natural (spontaneous) amenorrhea with an appropriate clinical profile (e.g. age appropriate, history of vasomotor symptoms) or have had surgical bilateral oophorectomy (with or without hysterectomy) or tubal ligation at least six weeks ago; in the case of oophorectomy alone, only when the reproductive status of the woman has been confirmed by follow up hormone level assessment is she considered not of child bearing potential.

Sexually active males must use a condom during intercourse while taking the drug and for 3 months after stopping study drug and should not father a child in this period; a condom is required to be used also by vasectomized men in order to prevent delivery of the drug via seminal fluid.

Patients unwilling or unable to comply with the protocol.

Prior treatment with a MET inhibitor or hepatocyte growth factor (HGF) targeting agent.

No history of another active cancer.

Human immunodeficiency virus (HIV) seropositivity.

Aspects of this application may be embodied in other forms or carried out in other ways without departing from the spirit or essential characteristics thereof. The present disclosure is therefore to be considered as in all aspects illustrated and not restrictive, and all changes which come within the meaning and range of equivalency are intended to be embraced therein.

What is claimed is:

1. A method of treating a cancer patient in need thereof, comprising administering to the patient a therapeutically effective amount of a catecholic butane and a therapeutically effective amount of a Met inhibitor, or an Alk inhibitor, wherein administration of the combination of the catecholic butane and the Met inhibitor or Alk inhibitor provides a synergistic therapeutic effect compared to each compound alone, and wherein the catecholic butane inhibits the tyrosine kinase activity of both IGF-1R and EGFR, and wherein the cancer is breast cancer, lung cancer, non-small cell lung cancer, pancreatic cancer, colon cancer, cervical cancer or neuroblastoma.

2. The method of claim 1, wherein the Met inhibitor is Cabozantinib, Tivantinib, Foretinib, Capmatinib (INCB28060), AMG-458, PF-04217903, Crizotinib (PF-02341066), Golvatinib (E7050), MK-2461, BMS-777607 or JNJ-38877605.

3. The method of claim 1, wherein the Alk inhibitor is Crizotinib, Ceritinib, or Alectinib (CH5424802).

4. The method of claim 1, wherein the proliferative disease is malignant, pre-malignant or benign cancer.

5. The method of claim 1, wherein said catecholic butane inhibits tyrosine kinase activity of IGF-1R, EGFR, cMet and/or KDR (VEGF2).

6. The method of claim 1, wherein said patient has a proliferative disease that is resistant to Erlotinib (TARCEVA®) or Gefitinib (IRESSA®), or who has relapsed after treatment with Erlotinib (TARCEVA®) or Gefitinib (IRESSA®).

7. The method of claim 4, wherein cancer cells contain a T790M mutation in an ATP binding domain of a receptor tyrosine kinase (RTK).

8. A method of treating a cancer patient that is resistant to Erlotinib (TARCEVA®) or Gefitinib (IRESSA®), comprising administering to the patient a therapeutically effective amount of a catecholic butane and a therapeutically effective amount of a Met inhibitor or an Alk inhibitor, wherein administration of said catecholic butane restores the effectiveness of cisplatin, Erlotinib (TARCEVA®) or Gefitinib (IRESSA®), and wherein the cancer is breast cancer, lung cancer, non-small cell lung cancer, pancreatic cancer, colon cancer, cervical cancer or neuroblastoma.

9. The method of claim 8, wherein said catecholic butane binds to the substrate-binding domain of a receptor tyrosine kinase (RTK) and induces a conformational change in the RTK.

10. The method of claim 8, wherein the Met inhibitor is Cabozantinib, Tivantinib, Foretinib, Capmatinib (INCB28060), AMG-458, PF-04217903, Crizotinib (PF-02341066), Golvatinib (E7050), MK-2461, BMS-777607 or JNJ-38877605.

11. The method of claim 8, wherein the Alk inhibitor is Crizotinib Ceritinib, or Alectinib (CH5424802).

12. The method of claim 1, wherein the catecholic butane comprises a catecholic butane of formula I, pharmaceutically acceptable salts thereof, pharmaceutically acceptable solvates thereof, metabolites thereof, tautomers thereof or prodrugs thereof:

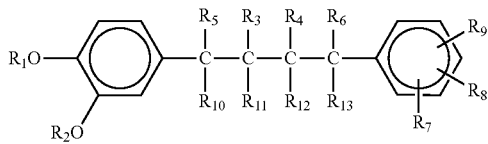

wherein R1 and R2 are independently H, lower alkyl, or lower acyl;
R3, R4, R5, R6, R10, R11, R12 and R13 are independently H or lower alkyl; and
R7, R8 and R9 are independently H, hydroxy, lower alkoxy or lower acyloxy.

13. The method of claim 1, wherein the catecholic butane is selected from the group consisting of NDGA, tetra-O-methyl NDGA; tetraglycinyl NDGA; tetra-dimethylglycinyl NDGA or a salt thereof; or tri-O-methyl NDGA; nordihydroguaiaretic acid tetrapivalate; nordihydroguaiaretic acid tetrapropionate and all optical configurations thereof.

14. The method of claim 1, wherein the catecholic butane is 1,4-bis(3,4-dihydroxphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; dihydroxyphenyl)-4-(3,4,5-trihydroxyphenyl)butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; or 1-(3,4-dihydroxyphenyl)-4-phenylbutane; 1-(3,4-dihydroxyphenyl)-4-(2,5-dihydroxyphenyl)butane.

15. The method of claim 1, wherein the catecholic butane is nordihydroguaiaretic acid (NDGA).

* * * * *